United States Patent [19]

Kempe et al.

[11] Patent Number: 4,661,450

[45] Date of Patent: Apr. 28, 1987

[54] MOLECULAR CLONING OF RNA USING RNA LIGASE AND SYNTHETIC OLIGONUCLEOTIDES

[75] Inventors: Tomas Kempe, Minnetonka; Anthony F. Purchio, Edina; Marc S. Collett; William J. DeLorbe, both of Minnetonka, all of Minn.

[73] Assignee: Molecular Genetics Research and Development Limited Partnership, Minnetonka, Minn.

[21] Appl. No.: 491,099

[22] Filed: May 3, 1983

[51] Int. Cl.[4] .................. C12P 21/00; C12P 19/34; C12N 1/20; C12N 1/00; C07H 15/12
[52] U.S. Cl. .................................... 435/172.3; 435/68; 435/91; 435/253; 435/317; 536/27
[58] Field of Search .......................... 536/27, 28, 29; 435/172.3, 68, 70, 317, 91

[56] References Cited

U.S. PATENT DOCUMENTS

| | | | |
|---|---|---|---|
| 4,237,224 | 12/1980 | Cohen et al. | 435/172.3 |
| 4,304,863 | 12/1981 | Collins et al. | 435/68 |
| 4,321,365 | 3/1982 | Wu et al. | 536/27 |
| 4,362,867 | 12/1982 | Paddock | 536/27 |
| 4,417,046 | 11/1983 | Hsiung | 536/27 |

OTHER PUBLICATIONS

Kempe et al, Nucl Acid Res, vol. 10, (21), 1982, "Selective 2'benzoylation of the cis, 2',3'diols of protected-ribonucleosides, New solid phase synthesis of RNA and RNA-DNA mixtures".
Emblad et al, Nucl Acid Res, vol. 10, (10), 1982, "Synthesis of Mixed Oligonucleotides Following the Solid Phase Method.
Okayama and Berg, 1982, Mol. Cell. Biol. 2: 161, "High-Efficiency Cloning of Full Length cDNA".
Gumport and Uhlenbeck, 1980, In "Gene Amplification and Analysis vol. II: Analysis of Nucleic Acid Structure by Enzymatic Methods", (J. G. Cirikjian and T. S. Papas, Eds.), Elsevier North Holland, Inc., N.Y.
Khorana, 1979, Science 203: 614, "Total Synthesis of a Gene".
Letsinger et al., 1967, J. Am. Chem. Soc. 89: 4801, "A Convenient Method for Stepwise Synthesis of Oligothymidylate Derivatives in Large-Scale Quantities".
Letsinger et al., 1976, J. Am. Chem. Soc. 97: 3278, "Phosphite Coupling Procedure Generating Internucleotide Links".
Letsinger et al., 1976, J. Am. Chem. Soc. 98: 3655, "Synthesis of Thymidine Oligonucleotides by Phosphite Triester Intermediates".
Ogilvie and Nemer, 1980, Canad. J. Chem. 58:(14): 1389, "The Synthesis of Oligoribonucleotides VI. The Synthesis of a Hexadecamer by Block Condensation Approach".
Ogilvie et al., 1977, J. Amer. Chem. Soc. 99: 7741, "Synthesis of Oligoribonucleotides".
Caruthers et al., 1980, Nucl. Acids, Res. Symposium Ser. 7: 215, "New Chemical Methods for Synthesizing Polynucleotides".
Crea and Horn, 1980, Nucl. Acids, Res. 8(10): 2331, "Synthesis of Oligonucleotides on Cellulose by a Phosphotriester Method".
Matteucci and Caruthers, 1980, Tetrahedron Lett. 21: 719, "The Synthesis of Oligodeoxypyrimidines on a Polymer Support".

(List continued on next page.)

Primary Examiner—Thomas G. Wiseman
Assistant Examiner—Robin Lyn Teskin
Attorney, Agent, or Firm—Pennie & Edmonds

[57] ABSTRACT

Methods and compositions for the insertion and molecular cloning of RNA in DNA cloning vectors are described. RNA molecules to be cloned are modified by the ligation of oligonucleotide linkers onto the termini of the RNA molecule using T4 RNA ligase. Such linkers may be composed of DNA, RNA, or mixtures of each and facilitate the insertion and ligation of the RNA species into a DNA cloning vector. The resulting recombinant vectors are used to transform host cells which provide for the generation of multiple DNA copies of the RNA molecule.

39 Claims, 17 Drawing Figures

OTHER PUBLICATIONS

Rammler and Khorana, 1963, J. Amer. Chem. Soc. 84: 1997, "Studies on Polynucleotides. XX. Amino Acif Acceptor Ribonucleic Acids (1). The Synthesis and Properties of 2′(or 3′)-O-(DL-Phenylalanyl)-Adenosin, 2′(or 3′)-O-(DL-Phenylalanyl)-Uridine and Related Compounds".

Chow and Kempe, 1981, Nucl. Acids Res. 9*12): 2807, "Synthesis of Oligodeoxyribonucleotides on Silica Gel Support".

Racaniello and Baltimore, 1981, Proc. Natl. Acad. Sci., U.S.A., 78:(8): 4887, "Molecular Cloning of Poliovirus cDNA and Determination of the Complete Nucleotide Sequence of the Viral Genome.

Racaniello and Baltimore, 1981, Science., 214: 916, "Cloned Polivurus Complementary DNA is Infectious in Mammalian Cells".

Rose, 1980, Cell 19: 415, "Complete Intergenic and Flanking Gene Sequences from the Genome of Vesicular Stomatitis Virus".

Sleigh et al., 1979, Nucleic Acids Res. 7: 879, "The Influenza Virus Haemagglutinin Gene: Cloning and Characterization of a Characterization of a Double-Stranded DNA Copy".

Imai et al., 1983, Proc. Natl. Acad. Sci., U.S.A., 80: 373, "Molecular Cloning of Double-Stranded RNA Virus Genomes".

Heiland and Gething, Nature 292: 851, "Cloned Copy of the Haemagglutin Gene Codes for Human Influenza Antigenic Determinants in *E. coli*".

Efstratiadis et al., 1976, Cell 7: 279, "Enzymatic in Vitro Synthesis of Globin Genes".

Efstratiadis et al., 1975, Cell 4: 367, "Full Length and Discrete Partial Reverse Transcripts of Globin and Chorion MRNAs".

Land et al., 1981, Nucl. Acids Res. 9: 2251, "5′-Terminal Sequences of Eucaryotic mRNA can be Cloned with High Efficiency".

Goeddel et al., 1979, Proc. Natl. Acad. Sci. U.S.A., 76: 106, "Expression in *Escherichia coli* of Chemically Synthesized Genes for Human Insulin".

Goeddel et al., 1979, Nature 281: 544, "Direct Expression in *E. coli* of a DNA Sequence Coding for Human Growth Hormone".

Itakura et al., 1977, Science 198: 1056, "Expression in *E. coli* of a Chemically Synthesized Gene for the Hormone Somatostatin".

Gough et al., 1979, Nucl. Acids Res. 6: 1557, "Protected Deoxyribonucleoside-3′-aryl Phosphodiesters as Key Intermediates in Polynucleotide Synthesis. Construction of an Isosonucleotide Analogous to the Sequence at the End of Rous Sarcoma Virus 35S RNA".

Gough et al., 1980, Nucl. Acids. Res. Symposium Ser. 7: 99, "Ribonucleotide and Ribonucleotide Derivatives in Polynucleltide Synthesis".

Gough et al., 1981, Tetrahedron Lett. 22: 5177, "Recovery and Recycling of Synthetic Units in the Construction of Oligodeoxyribonucleotides on Solic Supports".

Ogilvie and Nemer, 1980, Tetahedron Lett 21: 4159, "Silica Gel as Solid Support in the Synthesis of Oligoribonucleotides".

Alvardo-Urbina et al., 1981, Science 214: 270, "Automated Synthesis of Gene Fragments".

B = U, A^{BZ}, G^{BZ}, G^{IBU}, C^{BZ}

DMTR = 4,4-DIMETHOXYTRITYL

R - BENZOYL OR 3,4,5 TRIMETHOXYBENZOYL

B = U, A^{BZ}, G^{BZ}, G^{IBU}, C^{BZ}

DMTR = 4,4-DIMETHOXYTRITYL $R_1$ = BENZOYL OR 3,4,5-TRIMETHOXYBENZOYL $R_2$ = CL, -N(CH_3)_2, -N(CH=N / N=N)

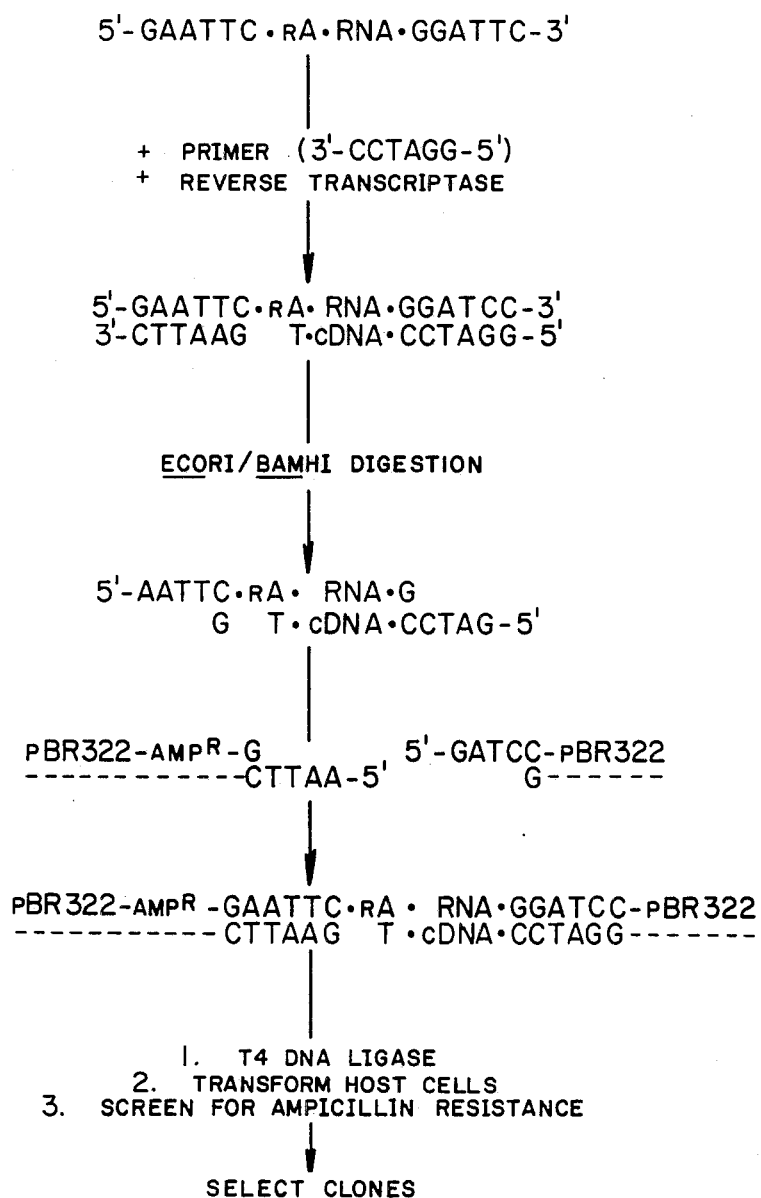

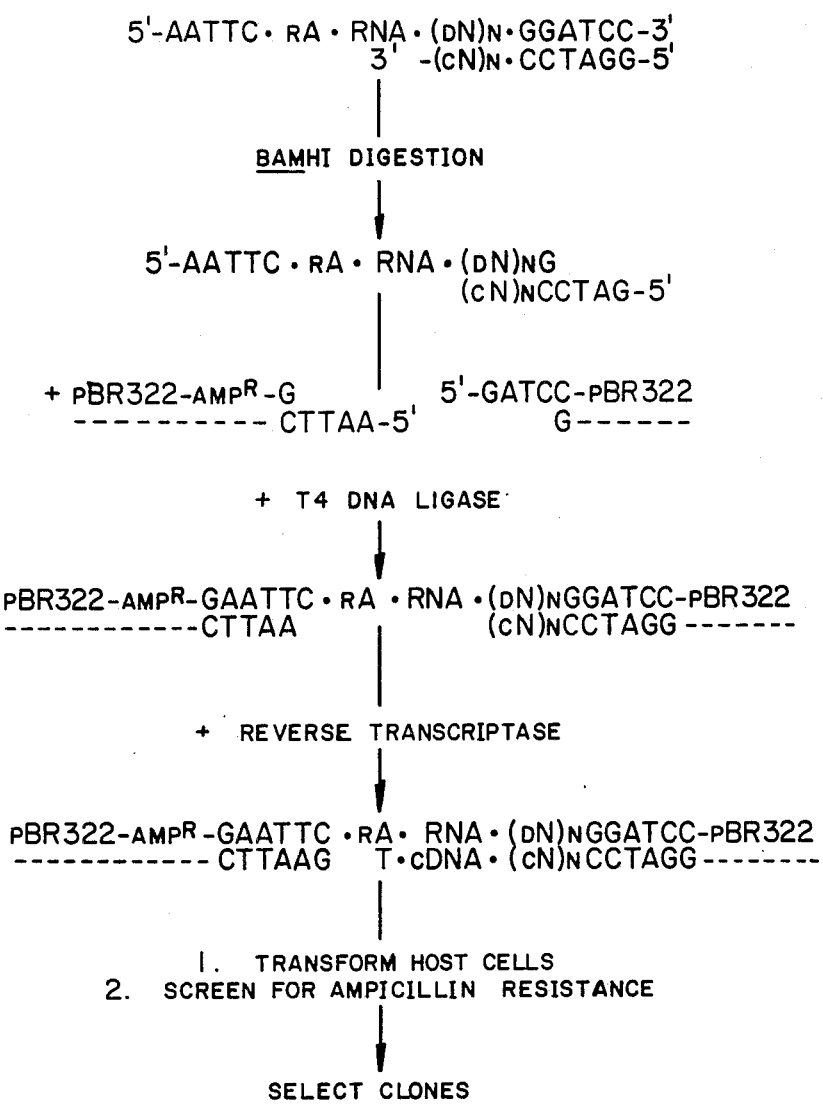

To FIG. 8B

MOLECULAR CLONING OF RNA USING RNA LIGASE AND SYNTHETIC OLIGONUCLEOTIDES

TABLE OF CONTENTS

1. Field of the Invention
2. Background of the Invention
   2.1. Recombinant DNA Technology
   2.2. T4 RNA Ligase
   2.3. Oligonucleotide Synthesis
3. Summary of the Invention
4. Brief Description of the Figures
5. Detailed Description of the Invention
   5.1. Synthesis and Modification of Linkers
      5.1.1. General Procedure for the Selective Benzoylation of the 2'-Hydroxyl Group of DMtr-Ribonucleosides
      5.1.2. General Procedure for the Functionalization of Silica
      5.1.3. General Procedure for the Preparation of 5'-O-(Dimethoxytrityl)-2'-O-(Benzoyl or 3,4,5-Trimethoxybenzoyl)-(U, rA$^{Bz}$, rG$^{Bz}$, rG$^{iBu}$ or rC$^{Bz}$)-3'-(N,N-Dimethylaminomethoxy)Phosphine
      5.1.4. Isolation of RNA and Mixed DNA-RNA from the Solid Silica Support
   5.2 Isolation and Preparation of the RNA Molecule for Linker Attachment
   5.3 T4 RNA Ligase Mediated Joining of Linkers to RNA
   5.4. Cloning the RNA
      5.4.1. Cloning RNA Flanked by Linkers Encoding Restriction Enzyme Sites
      5.4.2. Cloning RNA Flanked by Both Single- and Double-Stranded Linkers
      5.4.3. Cloning RNA Flanked by Single-Stranded Linkers
      5.4.4. Cloning RNA Possessing a 5'-Terminus Single-Stranded Linker
      5.4.5. Cloning RNA by Circularization
      5.4.6. Alternate Method for Cloning Polyadenylated RNA
6. Example: Molecular Cloning of β-Globin mRNA
   6.1. Synthesis of Linkers for Attachment to mRNA Termini
      6.1.1. Synthesis of Linkers for Attachmemt to the 5'-Terminus of the mRNA Molecule
      6.1.2. Modification of the ssDNA Linkers for Attachment to the 3'-Terminus of the mRNA Molecule
   6.2. Isolation of β-Globin mRNA
   6.3. Preparation of the β-Globin mRNA for DNA Linker Attachment
      6.3.1. Tobacco Acid Pyrophosphatase Treatment of β-Globin mRNA
      6.3.2. Treatment of the Decapped β-Globin mRNA with Bacterial Alkaline Phosphatase
      6.3.3. T4 Polynucleotide Kinase Treatment of β-Globin mRNA
   6.4. T4 RNA Ligase Mediated Covalent Linkage of ssDNA to β-Globin mRNA
      6.4.1. Joining the Synthetic DNA Linker to the 5'-End of the β-Globin mRNA
      6.4.2. Joining the Synthetic DNA Linker to the 3'-End of the β-Globin mRNA
   6.5. Cloning of β-Globin mRNA
      6.5.1. cDNA Synthesis
      6.5.2. Restriction Endonuclease Cleavage of the RNA/DNA Hybrid
      6.5.3. Restriction Endonuclease Cleavage of the DNA Cloning Vector
      6.5.4. Insertion of the β-Globin Gene into the DNA Cloning Vector
   6.6 Detection of Clones Containing cDNA Sequences
   6.7. Characterization of the Recombinant Plasmids Containing the β-Globin Gene
7. Example: Molecular Cloning of Rift Valley Fever Virus RNA
   7.1. Synthesis of the ssDNA Linker for Attachment to the 3'-Terminus of the RVF M-RNA
   7.2. T4 RNA Ligase Mediated Attachment of ssDNA Linker to RVF M-RNA
7.3. Cloning of RVF M-RNA

1. FIELD OF THE INVENTION

This invention relates to a process for the molecular cloning of RNA. Methods are provided for inserting modified RNA sequences into DNA cloning vehicles to form recombinant vectors which are then used to transform appropriate host cells so that multiple DNA copies of the recombinant vector are generated. The method of the present invention can be used for high efficiency cloning of RNA molecules such as mRNA or viral genomic RNA so that nearly full length copies of genetic sequences may be cloned; thus, the invention offers several advantages over existing cloning technologies.

While the methods disclosed may be used for cloning any RNA sequence of interest, it is demonstrated herein for cloning β-globin mRNA.

2. BACKGROUND OF THE INVENTION

2.1. RECOMBINANT DNA TECHNOLOGY

Current conventional methods used in recombinant DNA technology involve the insertion of specific DNA sequences into DNA vehicles (vectors) to form recombinant DNA molecules which are capable of replication in a host cell. Generally, though not necessarily, the inserted DNA sequence is foreign to the recipient DNA vehicle, i.e., the inserted DNA sequence and the DNA vector are derived from organisms which do not normally exchange genetic information in nature, or the inserted DNA sequence may be wholly or partially synthetically made. The first step in the recombinant DNA process is the isolation of the DNA sequences which encode the desired gene product. The second step involves the insertion of the isolated genetic sequence(s) into a DNA vector to form a recombinant DNA molecule capable of transforming single-cell hosts. Clones of host cell transformants generate multiple copies of the recombinant DNA vector, thus the inserted DNA sequence is "cloned".

In recent years several general methods have been developed which enable construction of recombinant plasmids. For example, U.S. Pat. No. 4,237,224 to Cohen and Boyer describes production of such recombinant plasmids using restriction enzymes and methods known as ligation. Synthetic oligonucleotides composed of DNA have been employed as linker molecules in cloning DNA. These DNA linker molecules, which can encode restriction endonuclease recognition sequences, are joined to the termini of the DNA molecule to be cloned and thus facilitate insertion into a DNA cloning vehicle (see U.S. Pat. No. 4,321,365).

The recombinant plasmids are then introduced into unicellular organisms by means of transformation. In other words, the recombinant plasmids produced by such conventional methods can be used to transform or "infect" cells in which the vector is compatible, resulting in introduction of the foreign gene into the cell. Because of the general applicability of the techniques described therein, U.S. Pat. No. 4,237,224 is hereby incorporated by reference into the present specification.

Another method for introducing recombinant plasmids into unicellular organisms is described by Collins and Hohn in U.S. Pat. No. 4,304,863 which is also incorporated herein by reference. This method utilizes a packaging/transduction system with bacteriophage vectors.

The recombinant DNA molecules must be capable of autonomous replication in the host cell and should have a marker function which allows for the selection of host cells so transformed. Culturing of the host cell transformants results in host cell replication of the recombinant plasmid and thus generates multiple copies of the DNA sequences. Furthermore, if all of the proper replication, transcription and translation signals are correctly arranged on the plasmid, the foreign gene will be properly expressed in the transformed cells and their progeny.

The controlled bacterial production of such polypeptide products as somatostatin [Itakura, et al., 1977, Science 198: 1056], the component α and β chains of human insulin [Goeddel, et al., 1979, Proc. Natl. Acad. Sci., U.S.A. 76: 106], and human growth hormone [Goeddel, et al., Nature 281: 544]has already been demonstrated. Production of other polypeptides which are in short supply, as well as viral proteins necessary for vaccine production, are within the capabilities of recombinant DNA technology.

Current methods in gene cloning require that both the gene and the vector exist as double-stranded linear DNA molecules; however, the genetic sequences used for cloning are often isolated in the form of RNA. For instance, when the genes of RNA viruses are sought to be cloned, the entire viral genome is isolated from purified virus, or virus-specific mRNA is isolated from virus-infected cells. Typically, gene sequences are retrieved from eucaryotic cells in the form of messenger RNA (mRNA).

Unlike procaryotic genes, many eucaryotic genes contain intervening sequences (introns) which are not present in the mature mRNA or the corresponding complementary DNA (cDNA) coding for the gene (for review see Chambon, 1981, Scientific American 244(5): 60-71). During mRNA processing, these introns are spliced out of the mRNA prior to translation (for reviews see Crick, 1979, Science 204: 264-271; Sharp, 1981, Cell 23: 643-646).

Isolation of mRNA as the gene source for cloning offers a distinct advantage since expression of eucaryotic genes cloned in procaryotic hosts requires that the coding sequence of the gene of interest be available in a form uninterrupted by intervening sequences. Thus the eucaryotic mRNA sequences, free of introns, are the preferable source of genetic material for cloning in procaryotes.

According to conventional methods, the isolated mRNA or viral RNA is transcribed into complementary DNA (cDNA) copies. The cDNA is then enzymatically processed into double-stranded DNA molecules which can be inserted into cloning vectors.

Such recombinant DNA techniques have been recently used for cloning cDNA copies of RNA viral genomes such as poliovirus (Racaniello and Baltimore, 1981, Proc. Natl. Acad. Sci., U.S.A. 78(8): 4887-4891; Racaniello and Baltimore, 1981, Science 214: 916-919); vesicular stomatitis virus (Rose, 1980, Cell 19:415-421); and influenza (Sleigh, et al., 1979, Nucleic Acids Res. 7: 879-893); and very recently, double-stranded RNA virus genomes such as rotavirus and reovirus (Imai et al., 1983, Proc. Natl. Acad. Sci., U.S.A. 80: 373-377). These techniques also have an application in the production of viral antigens for use in antiviral subunit vaccines (Heiland and Gething, 1981, Nature (London) 292: 851-852).

One difficulty encountered in cloning the cDNA copy of a gene is in the enzymatic processing of the cDNA molecule into a full length (or nearly full length) double-stranded form. Even if reaction conditions are adjusted to obtain complete cDNA copies of the mRNA, parts of the sequence may be lost during synthesis of the second DNA strand. Second strand synthesis requires the enzyme $E.$ $coli$ DNA polymerase I (Pol I) to utilize the single-stranded cDNA as both primer and template. This results in the formation of a double-stranded DNA molecule which has a single-stranded loop located at the terminus corresponding to the 5' terminus of the original mRNA molecule (Efstratiadis, 1976, Cell 7: 279-288). This single-stranded loop must be digested with S1 nuclease (an enzyme that preferentially degrades single-stranded DNA or RNA) before the double-stranded molecule can be inserted into a cloning vector. The S1 nuclease digestion, however, results in the removal of portions of the cDNA corresponding to the 5'-terminus of the mRNA molecule and reduces the yield of full length cDNA clones. Several modifications of this procedure which eliminate the need for S1 nuclease digestion have been reported (Land, et al.; 1981, Nucleic Acids Res. 9: 2251-2266). More recently, Okayama and Berg (1982, Molecular and Cellular Biology 2(2): 161-170) reported a method for inserting mRNA molecules into DNA cloning vectors which have been modified by oligo(dT) tailing, so that the 3'-poly(A) tail of the mRNA hybridizes to the oligo(dT) tail of the vector. After cDNA synthesis, the free ends of the plasmid and vector are modified to allow hybridization, and finally, ligation.

2.2. T4 RNA LIGASE

The enzyme T4 RNA ligase catalyzes the ATP-dependent formation of a phosphodiester bond between a 3'-hydroxyl nucleic acid acceptor and a 5'-phosphate nucleic acid donor. Thus, the enzyme is capable of catalyzing the ligation of two oligonucleotides or the circularization of a single oligonucleotide. In contrast to DNA ligase, T4 RNA ligase has a greater affinity for RNA substrates and does not require a complementary template strand to align donor phosphates with acceptor hydroxyls.

The minimal donor for the ATP-dependent T4 RNA ligase rection is a 3',5'-biphosphate (pNp); although a 5'-phosphate is essential for the formation of the phosphodiester bond, a phosphate 3' to the donor nucleoside is necessary as well. As a result 5'-phosphorylated oligonucleotides are appropriate donors.

The presence of a secondary or tertiary structure in an RNA donor molecule is postulated to inhibit the ligase reaction; thus the 5'-phosphate of yeast tRNA$^{Phe}$ is almost totally inactive as a donor. In contrast, DNA restriction fragments are good donors. In fact, little difference is observed between DNA restriction fragments which have 5'-staggered ends and those which have blunt ends.

The suitable minimal acceptor molecules for the T4 RNA ligase reaction are trinucleoside diphosphates. Although RNA and DNA are equally reactive as donors, DNA is a much less efficient acceptor than is RNA. In addition, the nucleotide composition of the acceptor greatly influences the efficiency of the RNA ligase reaction; oligo(A) seems to function as the most efficient acceptor. RNA molecules are excellent acceptors in the T4 RNA ligase reaction.

The presence of a secondary structure of an RNA acceptor molecule has little, if any, effect on the reaction. However, the 5'-cap structure (m$^7$G$^5$'ppp-5') of mRNA is neither an acceptor nor a donor for the T4 RNA ligase reaction.

RNA ligase has been used for the synthesis of oligonucleotides. Efficiency of the reactions can be enhanced by blocking the 3'-terminus of donor molecules and de-phosphorylating the 5'-terminus of the acceptor molecule; thus the reaction is driven to yield products containing a defined order of the oligonucleotide sequences. For a review of T4 RNA ligase properties and activity, see Gumport and Uhlenbeck, 1980, in "Gene Amplification and Analysis", Vol. II: Analysis of Nucleic Acid Structure by Enzymatic Methods, Chirikjian and Papas, eds. Elsevier North Holland, Inc.

In a very recent report (Imai, et al., 1983, Proc. Natl. Acad. Sci., U.S.A. 80: 373–377), T4 RNA ligase was used to attach homopolymeric ribonucleotide tails (oligo(C)$_{15}$) to the 3'-termini of double-stranded RNA molecules isolated from reovirus and rotavirus (double-stranded RNA viruses). These tailed double-stranded RNAs were separated and transcribed into cDNAs. The cDNAs were annealed to form double-stranded cDNA molecules which were inserted into pBR322 and cloned. As a result, some clones contained full-length copies of the virus genome segment.

2.3. OLIGONUCLEOTIDE SYNTHESIS

The Khorana diester method for DNA synthesis (H.G. Khorana, 1979, Science 203:614) was a major development in the synthesis of oligodeoxyribonucleotides. According to the diester method suitably protected mononucleotides are condensed to form a dideoxynucleotide containing a phosphodiester bond. A major disadvantage of the diester method is that several hours to several days are required for condensations. Additionally, the condensation product is a diester of phosphoric acid; therefore, the third functional group on the phosphate exists as an ionized acid in the form of a salt. These salts may be purified in only small quantities using a long and tedious procedure.

The triester method for DNA synthesis, as developed by Letsinger et al. (1967, J. Am. Chem. Soc. 89:4801), offered major improvements over the diester method. The triester method uses an extra protecting group, usually a chlorophenyl group, on the phosphate of the reactants and products. The direct product of condensation is a triester of phosphoric acid. Condensation times are shorter and purification of product is simplified because the oligonucleotide products are soluble in organic solvents. In a final step the phosphate blocking group is removed to yield the desired phosphodiester linkage. However this process offered little improvement in the rapid purification of the final product, the oligonucleotide sequence.

In a significant development, Letsinger et al., reported an improved phosphite triester procedure for generating internucleotide links based on the reactivity of phosphochlorides toward alcohols in tetrahydrofuran at low temperatures, and the simple oxidation of phosphites to phosphates by iodine and water (Letsinger, et al., 1975, J. Am. Chem. Soc. 97:3278; ibid 98:3655). Using this procedure a dinucleotide could be prepared in less than one hour. The phosphite triester approach has since been used and modified by Ogilvie (Ogilvie & Nemer; 1980, Can. J. Chem. 58 (14):1389) in the synthesis of oligoribonucleotides.

The phosphite triester method provided the possibility of synthesis of the oligonucleotide chains on insoluble supports such as silica or cellulose (Caruthers et al., 1980, Nucleic Acids Res. Symposium Ser. 7:215–223; Crea and Horn, 1980, Nucleic Acids Res. 8(10):2331; Matteucci and Caruthers, 1980, Tetrahedron Letters 21:719). Insoluble supports offer the advantage of ease in separation of reacted from unreacted components and the practicality of automation. Accordingly, the first unit of the oligonucleotide chain is attached to the insoluble support matrix. The second nucleoside of the chain and all necessary reagents are then added. All unreacted components are washed off with solvent at the end of each reaction period. These steps are repeated until the chain is complete at which time the chain is removed from the solid support.

Finally, Chow and Kempe (1981, Nucleic Acids Res. 9(12):2807–2817) reported a rapid solid phase method of oligonucleotide synthesis based on monomeric protected nucleosides which is herein incorporated by reference. The solid phase synthesis of oligonucleotides on silica gel described by Chow et al. uses monomeric base protected 5'-O-dimethoxytrityl-nucleoside-3'-O-methylphosphochlorides. They introduced an improved method for the functionalization of silica involving deprotection of the 5'-O-dimethoxytrityl group with zinc bromide/nitromethane/water, and the use of acetic anhydride in N,N-dimethylaminopyridine as a capping reagent. The synthetic oligonucleotides are first isolated as 5'-O-dimethoxytritylated compounds which are fully deprotected at the triester bond and at the purine/pyrimidine rings and are then purified by HPLC as fully deprotected oligodeoxynucleotides.

The major problem in the synthesis of RNA or mixed oligonucleotides (i.e., RNA-DNA mixtures) is in differentiating between the two hydroxyl groups of the cis 2',3'-diols of ribonucleosides. The relative reactivity between the two hydroxyl groups has been studied by many groups and in certain systems the 2'-hydroxyl group was demonstrated to have an enhanced reactivity over the neighboring 3'-hydroxyl group. Specific protection of the 2'-hydroxyl groups has been obtained through intermediates where the 5'- and 3'-hydroxyl groups were protected (e.g., diesters, 5',3'-cyclic phosphates, or cyclic 5,3'-disiloxanes, were used as intermediates leaving the 2'-hydroxyl group available for reaction). Early work in RNA chemistry focused on acyl and benzoyl protecting groups. These ester groups offered two advantages: (1) they were readily formed, and (2) they were easily removed under mildly basic conditions. However, the 2'-isomer easily converts to the 3'-isomer which appears to be more thermodynamically stable (Fromageot et al., 1967, Tetrahedron 23:2315).

Attempts to separate such compounds were reported not to be possible (Rammler and Khorana, 1962, J. Amer. Chem. Soc. 84:3112; ibid, 1963, J. Amer. Chem. Soc. 85:1997). Thus the presence of the 2'-hydroxyl group has hindered developments in oligoribonucleotide synthesis in that the protection reactions are tedious, the condensation reactions are slow and ultimate yields are low.

3. SUMMARY OF THE INVENTION

Methods and compositions are provided for the insertion of an RNA sequence into a DNA cloning vector to form a recombinant molecule that is used to transform appropriate host cells. Multiple copies of the recombinant molecule are generated during growth of the transformants.

According to the method of the present invention, the RNA molecules to be cloned are modified by the attachment of oligonucleotide sequences (linkers) to each terminus of the RNA. Depending upon the particular embodiment of the invention, these linkers may be composed of DNA, RNA or a mixture of DNA and RNA. The chemical procedures for the synthesis of these linkers are described in the present application and are disclosed in more detail by Kempe, et al., 1982, Nucleic Acids Res. 10(21): 6695.

The flanking oligonucleotide linkers may be designed to contain recognition sequences for restriction endonucleases; alternatively, the linkers may be homopolymers. As a result, the modified RNA molecule may be inserted into any appropriate DNA cloning vector with termini complementary to those on the RNA molecule. After annealing and ligating the modified RNA molecule to the cloning vector and after cDNA synthesis, the resulting recombinant molecules are used to transform appropriate host cells in which the recombinant molecules may be replicated. Multiple DNA copies of the recombinant molecule are generated during growth of the host cell transformants.

According to the method of the present invention, any RNA which can be isolated as either a single-stranded or a double-stranded molecule may be modified for insertion into any cloning vector, because any restriction site or homopolymeric tail may be linked to either end of the RNA molecule. Insertion of the modified RNA molecule directly into a cloning vector will also increase the yield of full length cDNA clones because second strand DNA synthesis occurs during replication of the recombinant plasmid.

4. BRIEF DESCRIPTION OF THE FIGURES

Unless otherwise indicated in the following figures, the linkers attached to each terminus of the RNA molecule (indicated by the filled in areas) may encode the same or different restriction enzyme sites. The use of different restriction sites at each terminus offers an advantage in that the RNA can be cloned in a directional manner. Of course, in each figure and example the linker may also comprise a homopolymer which is complementary to a homopolymeric tailed vector. The vector marker gene is denoted as "marker". The figures are not drawn to scale.

FIG. 3A is an example of the method of FIG. 2 wherein the RNA, flanked by single-stranded oligonucleotide liners, is inserted into the EcoRI and BamHI sites of pBR322.

FIG. 4A represents an example of the method of FIG. 3 wherein the RNA is inserted into the EcoRI and BamHI sites of pBR322.

Figure 7:
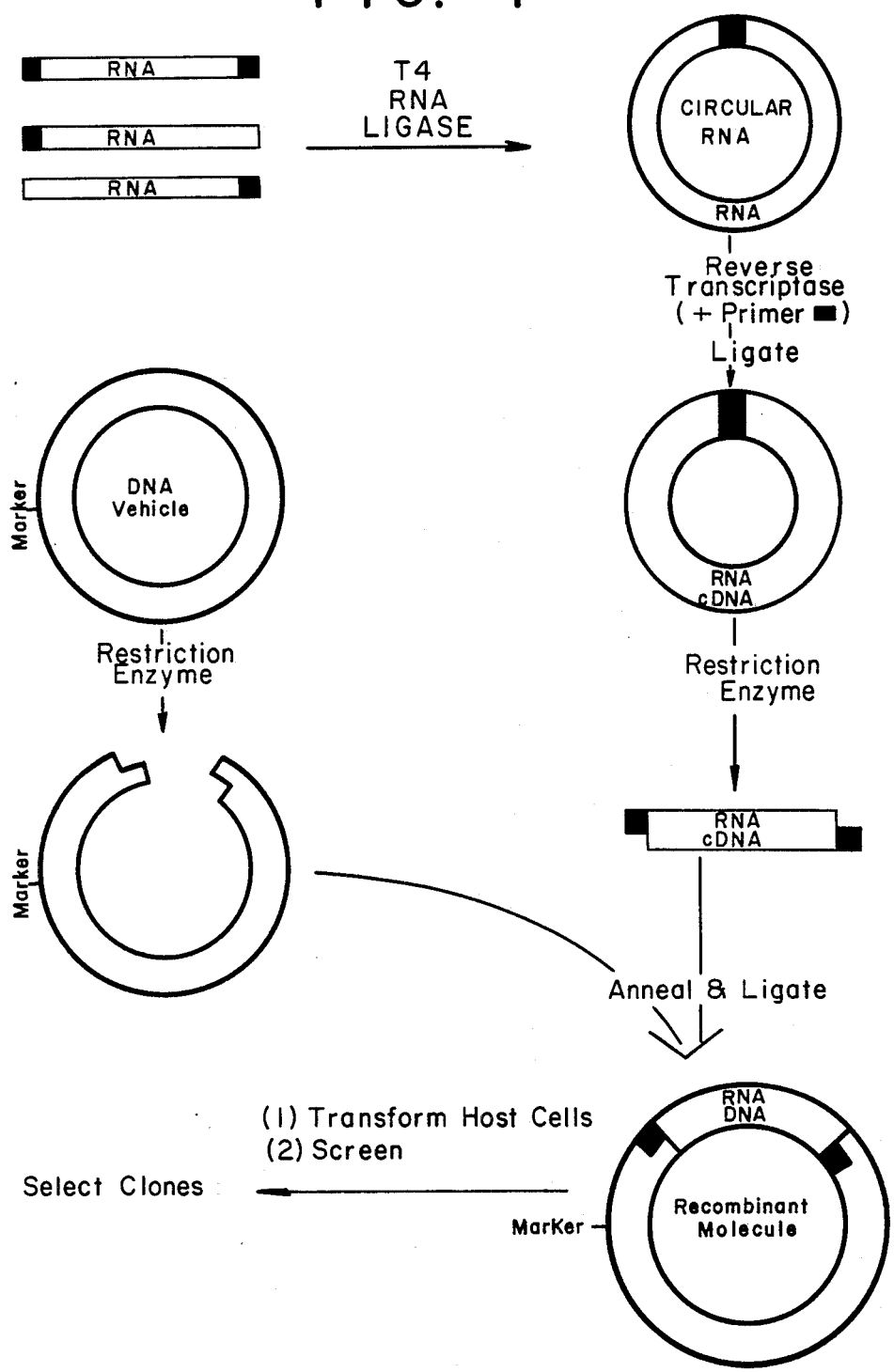

FIG. 7 is a schematic representation of a general method for cloning RNA by circularization. The RNA may be flanked by either or both 5'-terminus and 3'-terminus oligonucleotide linkers. Furthermore, the linkers may be single-stranded or double-stranded and may encode any desired restriction enzyme site.

Figure 7A:
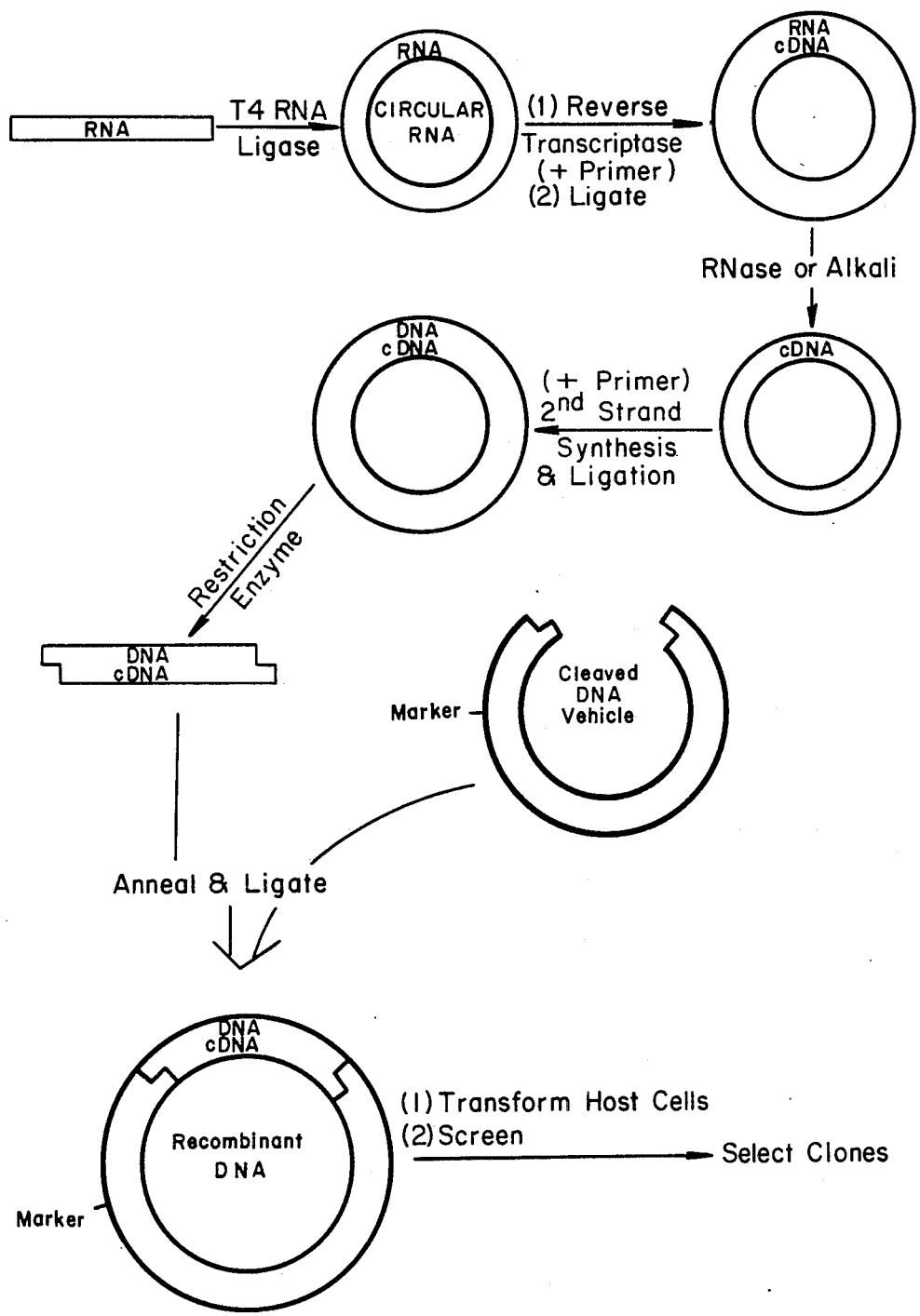

FIG. 7A is a schematic representation of cloning RNA by circularization wherein no linkers are attached to either end of the RNA molecule.

Figure 8A:
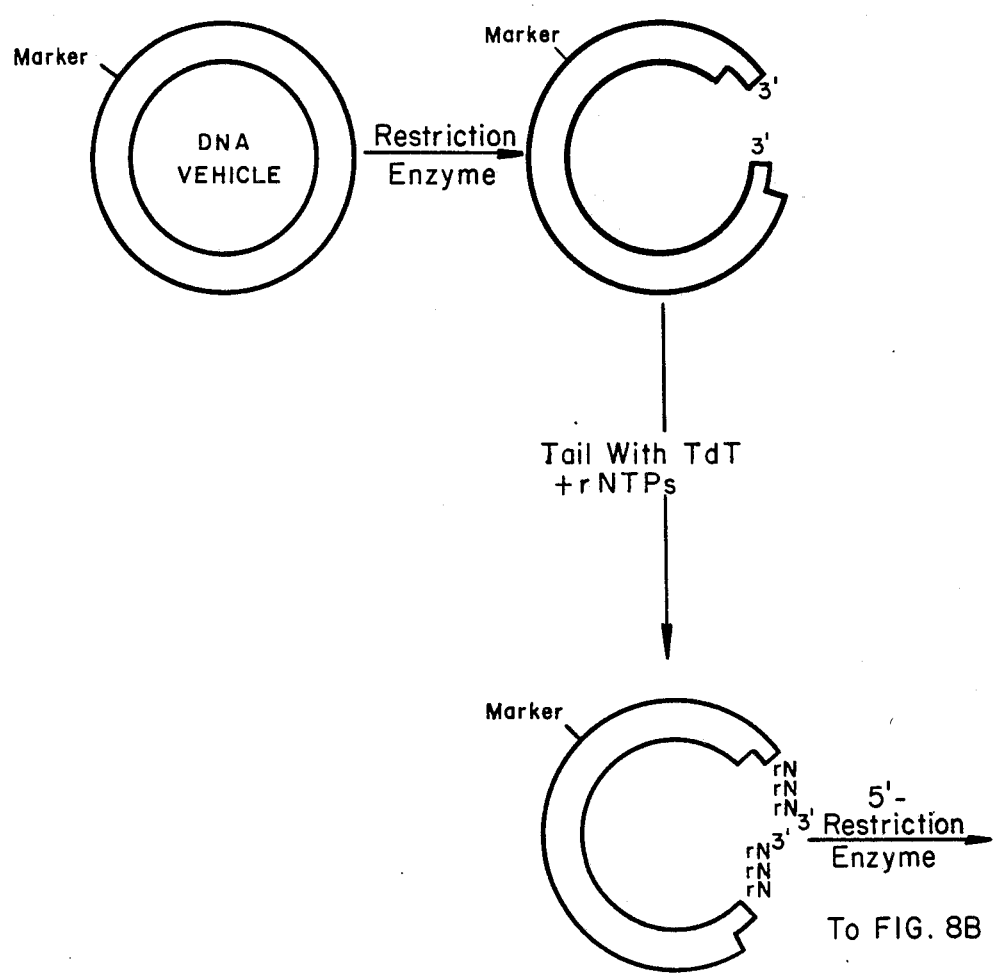
Figure 8B:
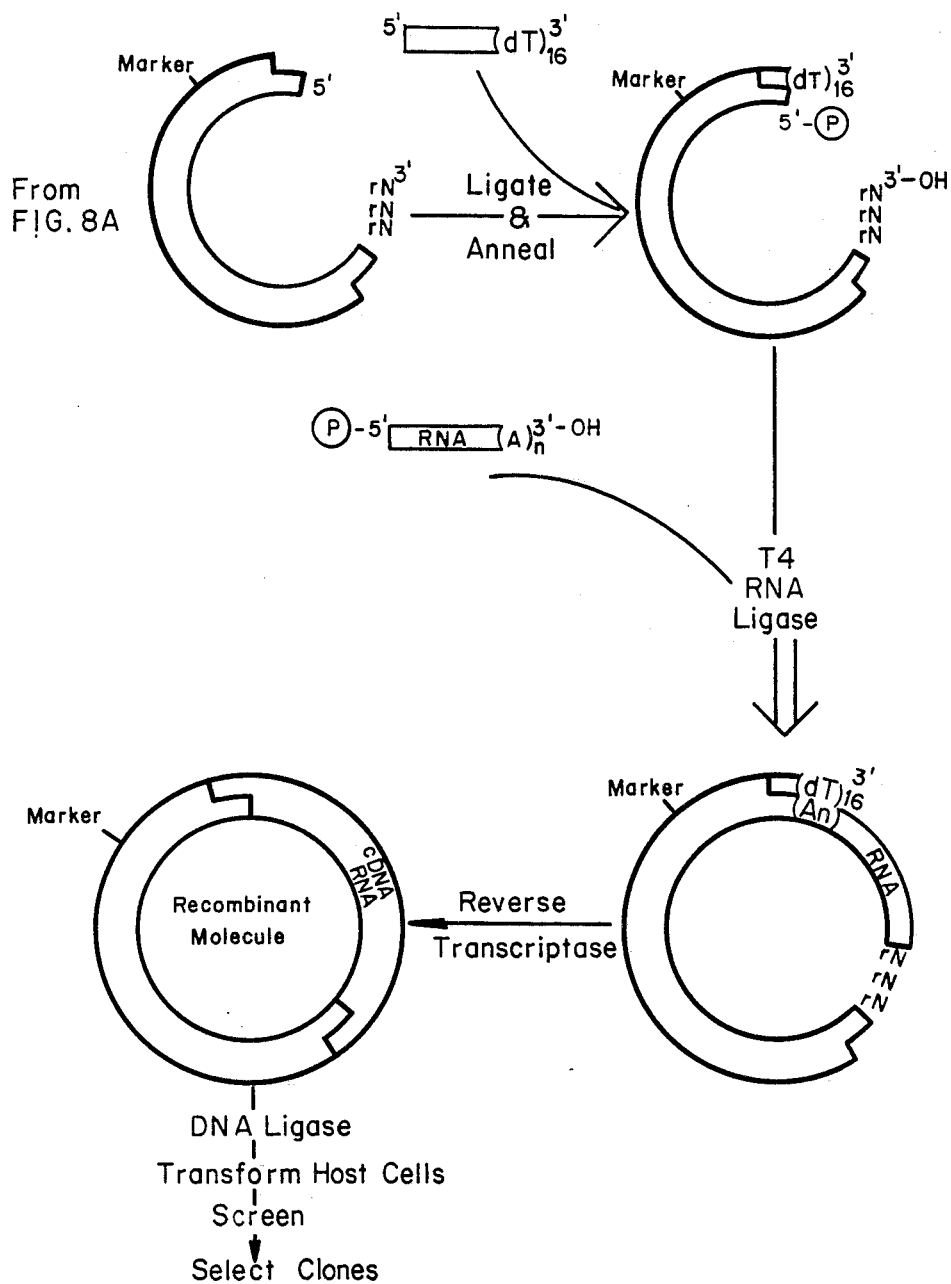

FIG. 8 is a schematic representation of an alternate method for cloning RNA using T4 RNA ligase wherein the vector itself is tailed with ribonucleotides.

5. DETAILED DESCRIPTION OF THE INVENTION

The methods described herein allow for the cloning of RNA in a DNA cloning vector to form recombinant molecules which contain full length RNA sequences.

The resultant recombinant molecules are capable of transforming appropriate host cells which are then able to produce multiple DNA copies of the RNA sequences.

The overall strategy of the present invention is to attach oligonucleotide linkers to the termini of a modified RNA molecule; such attachments may be accomplished via an RNA ligase reaction. Any RNA ligase may be used (e.g., RNA ligases of T-even bacteriophages). However, T4 RNA ligase activity has been more fully characterized than the activity of other RNA ligases, therefore, the invention is described in terms of using T4 RNA ligase.

The nucleotide sequences of the linkers are designed to encode restriction enzyme recognition sequences or cohesive termini or, alternatively, homopolymeric tails. These cohesive termini or tails allow for the insertion of the RNA into a DNA cloning vector possessing complementary termini, i.e., complementary cohesive termini or complementary homopolymeric tails. The insertion of the RNA into the DNA cloning vector occurs via base-pair hybridization (annealing) of the nucleotide sequences which flank the modified RNA molecule to the complementary single-stranded DNA (ssDNA) termini of the DNA cloning vector. The resultant recombinant molecules may then be ligated and used to transform appropriate host cells. As in most cloning strategies, the cloning vector chosen should possess a marker function gene so that host cells can be screened to permit the identification and selection of transformants. Ideally, the insertion site on the vector should not be necessary for marker function.

According to the method of the invention, the enzyme T4 RNA ligase is employed to covalently attach oligonucleotide linkers to either or both termini of an RNA molecule. Based on the particular embodiment of the invention, the linkers may be composed of deoxyribonucleotides, ribonucleotides, or mixtures of each. Depending upon the site of attachment to the RNA molecule to be cloned, i.e., whether the linker is to be attached to the 3'-acceptor terminus or to the 5'-donor terminus of the RNA molecule, the nucleotide composition of the linker is varied according to the requirements and constraints of the activity of T4 RNA ligase (explained below).

The ligase reactions may be carried out in any order, i.e., linker ligation to the 5'-terminus of the RNA may be accomplished before or after ligation to the 3'-terminus. However, depending on the composition of the RNA (e.g., mRNA, viral RNA, etc.) and the composition of the linkers (e.g., DNA, RNA or a mixture of each) both the oligonucleotide linkers and the isolated RNA may require modification before the T4 RNA ligase-mediated reaction is accomplished.

The enzyme T4 RNA ligase catalyzes the ATP-dependent ligation of a 5'-phosphoryl terminated nucleic acid donor to a 3'-hydroxyl terminated nucleic acid acceptor. In contrast with DNA ligases, RNA ligase has a preference for RNA substrates and does not require a complementary template strand to align the donor phosphate with the acceptor hydroxyl before catalyzing the reaction. As discussed previously (Section 2.2), 5'-phosphate DNA molecules (single or double-stranded) or RNA molecules (single-stranded only) are suitable donors, and 3'-hydroxyl RNA molecules are suitable acceptors, however, 3'-hydroxyl DNA molecules are poor acceptors. In addition, the mRNA (or viral RNA) cap structure ($m^7G^{5'}ppp^{5'}$-) is neither an acceptor nor a donor for the T4 RNA ligase reaction.

Due to the constraints of the T4 RNA ligase reaction, the linkers which are attached to the 5'-donor terminus of the RNA molecule should be efficient acceptor molecules, therefore the composition of these linkers includes but is not limited to: RNA, DNA.rN, DNA.RNA, or RNA.DNA.rN (in other words, any oligonucleotide which terminates with a ribonucleotide at its 3'-hydroxyl terminus).

The linkers which are attached to the 3'-acceptor terminus of the RNA molecule must be efficient donors, as a result these linker compositions allow for more flexibility and may be composed of either DNA, RNA or any mixture of the two; in fact, in certain embodiments described herein no linker is attached to the 3'-terminus of the RNA molecule or, alternatively, poly A polymerase may be used to attach a poly(A) tail to the 3'-terminus of the RNA molecule.

Finally, double-stranded DNA (dsDNA) linkers are suitable donors in the T4 RNA ligase reaction. Therefore, dsDNA linkers, or DNA restriction fragments possessing either blunt or 5'-staggered ends, or a cleaved DNA vector possessing a blunt or 5'-staggered end may be ligated to the 3'-terminus of the RNA molecule sought to be cloned. However, since DNA is a poor acceptor in the T4 RNA ligase reaction, the double-stranded DNA linkers to be used as acceptors should be mixed DNA.RNA molecules as described above.

It may be necessary to modify either or both the linkers and the RNA molecule used in the invention. For example, in order to make an mRNA an effective donor the 5'-cap must be removed and replaced with a 5'-phosphate (the same is true for capped viral RNAs).

Another linker modification may involve phosphorylation. When a linker is to be attached to the 3'-hydroxyl terminus of the RNA molecule via a T4 ligase reaction, it is necessary to first phosphorylate the 5'-terminus of the linker so that the molecule functions as a donor. Such phosphorylation may be accomplished using T4 polynucleotide kinase which catalyzes the transfer of the γ-phosphate group of ATP to the 5'-hydroxyl terminus of an oligonucleotide.

Finally, the nucleotide composition of the linker may require modification. Attachment of a linker to the 5'-terminus of RNA requires that the linker act as an acceptor molecule in the T4 RNA ligase reaction. Since DNA is a very poor acceptor, a DNA linker may have at least one or more ribonucleotides attached to the 3'- or 5'-terminus (e.g., DNA.rA). This may be accomplished using the solid phase synthesis method described by Kempe, et al. (infra).

Ultimately, the composition and sequence of the DNA linkers which flank the RNA molecule determine the method used to insert the RNA molecule into a DNA cloning vector.

The following description and accompanying figures will clarify and explain the method of the invention.

5.1. SYNTHESIS AND MODIFICATION OF LINKERS

The linkers used in the present invention may be synthesized by any method that can be utilized for the synthesis of mixed oligonucleotides in a defined sequence. A preferred method involves the solid phase synthesis of DNA, RNA, or DNA-RNA mixtures as described by Kempe, et al., 1982, Nucleic Acids Res.

10(21): 6695. However, other methods involving either solid phase synthesis or solution chemistry may be used. For example, see: Gough, et al., 1979, Nucleic Acids Res. 6: 1557; Gough, 1980, Nucleic Acids Res. Symposium Ser. 7: 99; Gough et al., 1981, Tetrahedron Lett., 4177; Ogilvie, et al., 1977, J. Amer. Chem. Soc. 99(23): 7741; Ogilvie and Nemer, 1980, Can. J. Chem. 58(14): 1389; for a review of oligonucleotide synthesis see Alvarado-Urbina, 1981, Science 214: 270. Depending upon the cloning strategy used in the present invention the nucleotide sequences of the synthetic linkers may be homopolymeric or may be designed to code for restriction enzyme sites or restriction enzyme staggered (cohesive) ends. Furthermore, the synthetic linkers may be single-stranded or double-stranded oligonucleotides.

The major problem in the synthesis of RNA or mixed oligonucleotides is the prevention of the formation of 2′-5′linkages during synthesis. The method of choice for synthesis of mixed oligonucleotides (Kempe, supra) involves using 5′-O-(Dimethoxytrityl)-2′-O-(benzoyl or 3,4,5-trimethoxybenzoyl)-base protected ribonucleosides which have been prepared by selective benzoylation of the 2′-hydroxyl group. The protected nucleosides are then converted to either methylphosphochloridites or methylphosphoamidites and are used to synthesize oligonucleotides on a silica gel solid support. Thus, RNA synthesis follows the same synthetic scheme presently employed in DNA chemistry and results in 3′-5′ linkages.

The synthetic oligonucleotides (DNA, RNA, or a mixture of each) are deprotected and isolated using conditions that minimize internucleotide cleavage. The use of 2′-benzoates as protecting groups for ribonucleosides makes it possible to easily prepare and isolate mixtures of DNA and RNA. When using these methods, benzoylation of 5′-O-tritylated, base-protected ribonucleosides is very selective for the 2′-hydroxyl group even at room temperature, and the products are stable under proper conditions. In addition to the high degree of selectivity in a protection reaction, the 2′-benzoate is stable against isomerization and hydrolysis during the phosphorylation of the 3′-hydroxyl group and against the chemicals used in the solid phase synthesis. The ester group is readily removed together with the base protecting groups giving a dimethoxy tritylated oligomer which could be isolated and detritylated to give the fully deprotected RNA by HPLC purification; thus the same purification steps presently used in DNA chemistry are followed; see Chow, Kempe, and Palm, 1981, Nucleic Acids Res. 9(12): 2807; Matteucci and Caruthers, 1980, Tetrahedron Lett. 21: 719.

Using the procedures described below, benzoylation of the protected ribonucleoside, DMTr-U, in pyridine at −45° C. or in dichloromethane/pyridine at −78° C. using one equivalent of benzoyl chloride yielded 2′/3′-benzoates in the ratio of 99:1. Under the same reaction conditions, using instead, 1.1 equivalents of benzoylchloride, the 2′-isomeric purity was 99% for DMTr-U and greater than 96% for the other ribonuclosides. The 10% excess reagent served to drive the reaction to completion. Therefore, treatment with 10% excess benzoyl chloride appears to be the method of choice for selective 2′-benzoylation; the 2′-benzoylated ribonucleotides are then coupled to silica. The subsequent solid phase synthesis of ribonucleotide chains, and mixed nucleotide chains may be accomplished via a modified phosphite method by the addition of 3′-phosphochloridite or 3′-phosphoamidite derivatives of the 2′-benzoylated ribonucleotides, and results in 3′-5′linkages (see Kempe et al., 1982, Nucleic Acids Res. 10: 6695-6714; Chow et al., 1981, Nucleic Acids Res. 9: 2807-2817 which are herein incorporated by reference and Section 6.1 infra).

5.1.1. GENERAL PROCEDURE FOR THE SELECTIVE BENZOYLATION OF THE 2′-HYDROXYL GROUP OF DMTr-RIBONUCLEOSIDES

Figure 1A:
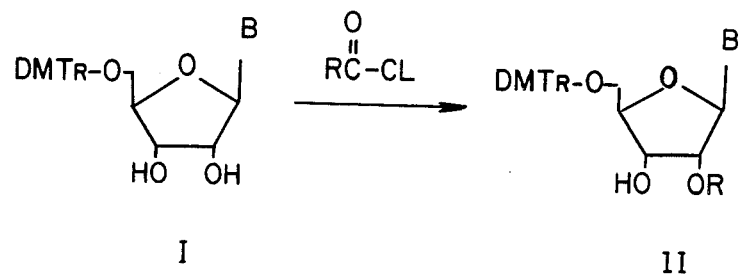
FIG. 1A is a schematic representation of the protection of the 2'-hydroxyl group of DMTr-ribonucleotides.

See FIG. 1A for a schematic representation of this reaction. The 5′-O-(dimethoxytrityl) base-protected ribonucleoside (U, rA$^{Bz}$, rG$^{Bz}$, rG$^{iBu}$ or rC$^{Bz}$, 10 mM) was coevaporated with dry pyridine (3×100 ml) in a 250 ml round bottom flask. In the third coevaporation, the volume was reduced to 50 ml. The round bottom flask was equipped with a rubber septum and magnetic stir bar and cooled to −45° C. with a dry ice-acetone-water bath. A solution of benzoyl chloride (11 mM, 1.3 ml) in dichloromethane (4 ml) was slowly added to the stirred mixture. A 20% excess of benzoyl chloride (12 mM, 1.4 ml) was used in the benzoylation of DMTr-rG$^{Bz}$ and DMTr-rG$^{iBu}$. After 30 minutes the reaction mixture was warmed to −20° C. and allowed to react at that temperature for 2 hours. The mixture was analyzed on TLC using 10% MeOH/CH$_2$Cl$_2$; the TLC was usually eluted first with Et$_2$O to remove pyridine. In general, the starting material was consumed after this reaction period. The mixture was quenched with water (0.5 ml) and then concentrated at reduced pressure at 30° C. to a gum. The gum was taken up in dichloromethane (250 ml) and washed with water (2×100 ml). The organic phase was dried over sodium sulfate and concentrated. The residue was dissolved in dichloromethane (30 ml) and the product was obtained by precipitation from hexane (1 l). The precipitate was filtered and dried in a dessicator over phosphorous pentoxide. This work up procedure minimized isomerization of the 2′-benzoate. Traces of the 3′-benzoate were detected by analysis on analytical C-18 HPLC.

The corresponding 2′-trimethoxybenzoate was obtained following this procedure using 1.1 equivalents of 3,4,5-trimethoxybenzoyl chloride in dichloromethane with 5 equivalents of pyridine at −78° C. The reaction was quenched with methanol at −78° C.

5.1.2. GENERAL PROCEDURE FOR THE FUNCTIONALIZATION OF SILICA

Porasil C (88 g) and triethoxysilylpropylamine (65 ml) in toluene (300 ml) were refluxed for 7 hours in a 1 l round bottom flask. The silica was then filtered and washed with pyridine (3×50 ml) and transferred to a 500 ml round bottom flask containing pyridine (100 ml). Trimethylsilylchloride (60 ml) was added and the mixture was shaken at room temperature for 1 hour. The silica was filtered and washed with the following: pyridine (2×100 ml), water (100 ml), pyridine (2×100 ml), pyridine-triethylamine (9:1, 50 ml), pyridine (2×100 ml) and ether (3×100 ml). The silica was dried in a dessicator at reduced pressure. The aminated silica (10 g) was functionalized with either succinylated deoxyribonucleosides or succinylated 2′-benzoylated ribonucleosides using the following procedure. The succinylated nucleoside (4 mM) was dissolved in DMF (10 ml) with N-hydroxybenztriazole (10 mM, 1.4 g) and treated with dicyclohexylcarbodiimide (20 mM, 4.1 g) in DMF (10 ml). (DMF was distilled under N$_2$ from CaH$_2$ prior to use.) The dicyclohexylurea formed during the active ester formation precipitated out of solution. The product mixture was centrifuged in a sealed serum bottom. The supernatant was removed and was added with a syringe to the silica (10 g) in pyridine (14 ml). The mixture was shaken at room temperature for 3 hours. The silica was filtered, washed with pyridine (3×50 ml) and then treated with the capping solution used in the solid phase synthesis. A mixture of solutions A and B, 1:1, v/v (20 ml) was added to the silica in a sintered glass funnel and was allowed to react for 10 minutes at room temperature with gentle agitation. The reagent was filtered off and the silica was washed with pyridine (3×50 ml) and ether (3×50 ml). After drying in a dessicator under reduced pressure, the silica was ready for use in solid phase synthesis. The functionalization was in the range of 0.005–0.008 mM/100 mg silica.

5.1.3. GENERAL PROCEDURE FOR THE PREPARATION OF 5'-O-(DIMETHOXYTRITYL)-2'-O-(BENZOYL OR 3,4,5-TRIMETHOXYBENZOYL)-(U, rA$^{Bz}$, rG$^{Bz}$, rG$^{iBu}$ or rC$^{Bz}$)-3'-(N,N-DIMETHYLAMINOMETHOXY)-PHOSPHINE

Figure 1B:
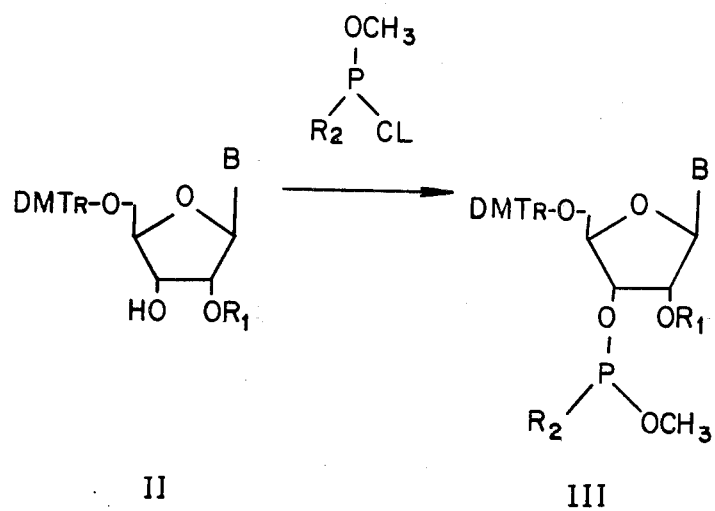
FIG. 1B is a schematic representation of the phosphorylation of the protected ribonucleotides.

See FIG. 1B for a schematic representation of this reaction. An oven-dried 50 ml flask (e.g., a serum bottle, Wheaton) containing a magnetic stir bar was flushed with dry argon and sealed with a teflon/silicon septum. Dry tetrahydrofuran, (THF, 20 ml) was added through a syringe and the solution was cooled to −78° C. with a dry ice-acetone bath. To the stirred solution was added chloro-N,N-dimethylaminomethoxyphosphine (3 mM, 0.35 ml) and triethylamine (3.6 mM, 0.48 ml). A solution of the protected ribonucleoside (3 mM) dissolved in THF (10 ml) was added to the cooled mixture of phosphorylating agent. Triethylammonium hydrochloride immediately formed and precipitated out of solution. After 30minutes the reaction mixture was removed from the cold-temperature bath and the hydrochloride was sedimented by centrifugation. The supernatant was transferred to a rubber septum-equipped round bottom flask containing dry toluene (100 ml). The product mixture was concentrated at reduced pressure at 30° C. To the dry residue (nucleoside phosphoamidite) was added another portion of toluene (3×100 ml) and the evaporation was repeated to remove excess triethylamine. The residue was dissolved in dichloromethane (6 ml) and precipitated from hexane (80 ml) cooled to −20° C. in a sealed serum bottle. The precipitate was sedimented by centrifugation and the solvent removed. The precipitate was dried at reduced pressure in a dessicator over phosphorous pentoxide. The amidite was dissolved in acetonitrile at a concentration of 1 mM/20 ml.

5.1.4. ISOLATION OF RNA AND MIXED DNA-RNA FROM THE SOLID SILICA SUPPORT

The final step in the solid phase synthesis was a THF wash of the silica support in the reaction column (HPLC precolumn with 1/16-inch end fittings, I.D. 3.2 mm, O.D. ¼-inch, length 50 mm). The silica was emptied from the column into a 7-ml vial and dried in a dessicator at reduced pressure. The support containing the synthetic oligonucleotide was treated with thiophenol-triethylaminedioxane (1:2:2, v/v, 1 ml) for 1.5 hours at room temperature. The reagent was removed from the support by filtration through a pasteur pipet with a silylated glass wool plug. The support was washed with dioxane (4×2 ml) and water (2×2 ml). After the washes, the support was transferred to a second vial and treated with concentrated aqueous ammonia (3 ml) for 1 hour at room temperature to cleave the oligonucleotide from the support. The aqueous phase was transferred to a polypropylene tube and concentrated at reduced pressure in a Speed-Vac concentrator (Savant). (When pure DNA was deprotected, the ammonia solution was transferred to another vial and heated for 5 hours at 50° C.) To the dried sample was added BuNH$_2$-MeOH-dioxane (1:1:2, v/v, 1 ml) and the sealed tube was heated at 40° C. for 7 hour. The deprotecting reagent was removed by concentration at reduced pressure. The DMTR-oligomer thus obtained was dissolved in water (0.5 ml) and separated by analytical or semipreparative C-18 HPLC. The isolated sample was concentrated and detritylated with 80% acetic acid-water (0.5 ml) for 10 minutes at room temperature. The solution was concentrated at reduced pressure and the residue taken up in water (0.3 ml). The fully deprotected oligomer was purified by C-18 HPLC. The purified sample was evaporated to dryness and stored at −20° C.

5.2. ISOLATION AND PREPARATION OF THE RNA MOLECULE FOR LINKER ATTACHMENT

Viral RNA may be isolated and purified by standard techniques. For instance, virus may be concentrated from infected cell culture fluids by rate-zonal sedimentation in sucrose gradients. RNA can be extracted from purified virions using hot phenol-chloroform. Finally, the RNA can be precipitated using ethanol.

Like mRNA, many viral genomic RNA molecules possess a 5'-cap structure. Furthermore, a number of viral genomic RNA species have proteins associated with the 5'-terminus. Depending upon the composition and structure of the viral RNA genome, the termini of the RNA molecule may have to be modified so that the RNA is a suitable substrate for the T4 RNA ligase reactions used in the practice of the present invention; i.e., the 5'-terminus of the molecule should function as an efficient donor and the 3'-terminus should function as an efficient acceptor.

According to the method of the present invention, the gene sought to be cloned may be isolated in its mRNA form. Any of the standard methods (e.g., phenol-chloroform extraction) may be used to extract and isolate RNA from lysates of cells which express the gene sought to be cloned. The mRNA component may be isolated and purified from the cell lysate RNA using immobilized oligo(dT) which hybridizes to the poly(A) tail of mRNAs. For a compilation of laboratory protocols for the extraction and purification of mRNA from eucaryotic cells, see Maniatis, et al., 1982, Molecular Cloning—A Laboratory Manual, Cold Spring Harbor Laboratory, pages 187–201.

Since RNA molecules can function as acceptors and donors, properly prepared mRNA species or viral genomic RNA molecules are suitable substrates for the T4 RNA ligase reactions used in the practice of the invention. However, as previously mentioned, the m$^7$G$^{5'}$-ppp$^{5'}$-RNA cap structure will not function as a donor. Thus, most isolated mRNA molecules and many viral RNA molecules must be decapped and modified to contain a single phosphate at the 5'-terminus in order to function as a donor molecule. According to the present invention, the 5'-terminus of the RNA molecule may be modified before or after a linker is attached to the 3'-terminus of the RNA molecule.

One method for preparing the 5'-terminus of a capped RNA is to treat the capped viral RNA or mRNA with tobacco acid pyrophosphatase (TAP) to remove the 5'-cap structure. This results in a mixture of 5'-mono- and 5'-di-phosphate RNAs. Treatment with the enzyme bacterial alkaline phosphatase removes the 5'-phosphate groups and results in a 5'-hydroxyl terminus. Finally, the enzyme T4 polynucleotide kinase may be used to transfer the γ-phosphate of dATP to the 5'-hydroxyl terminus of the decapped, dephosphorylated RNA molecule. The phosphorylation may be accomplished after linker ligation to the RNA 3'-terminus. Alternatively, the RNA may be used directly after incubation with TAP since prolonged treatment with this enzyme leaves predominantly 5'-monophosphate on RNA molecules.

If the RNA molecule is a viral RNA species that has a protein associated with the 5'-terminus, the protein should be removed so that the 5'-terminus of the RNA molecule can function as an efficient donor in the T4 RNA ligase reaction. If the protein is attached to the 5'-terminus non-covalently, then treatment of the RNA species with hot phenol (a step accomplished during the purification of the RNA) will effectively remove the protein. However, if the protein is covalently attached to the 5'-terminus of the RNA molecule, the protein may be removed by treatment with a protease (e.g., protease K). Thus, the protein will be degraded but the RNA molecule itself will remain unaffected. Once so modified, the resulting RNA molecule may now serve as either a donor or acceptor in the T4 RNA ligase mediated ligation of the oligonucleotide linkers to the RNA molecule.

It should be noted that secondary and tertiary structure of RNA molecules inhibits the ability of the RNA molecules to function as donors in the T4 RNA ligase mediated reaction (this inhibition is not observed when the donor molecule is DNA). As a result, when the RNA molecule is to be used as a donor (especially viral genomic RNA), it may be desirable to adjust the reaction conditions to minimize the formation of secondary and tertiary structures (e.g., folding of the molecule, double-stranded RNA, etc.). This may be accomplished by adding a suitable denaturant (e.g. DMSO, dimethylsulfoxide; methyl mercuric hydroxide; etc.) to the reacton mixture to inhibit the formation of secondary structure in the RNA molecule.

5.3. T4 RNA LIGASE MEDIATED JOINING OF LINKERS TO RNA

The properties of the donor and acceptor molecules of the T4 RNA ligase reaction enable one to adjust reaction conditions to favor the desired reaction product which is an RNA molecule flanked by linkers. Thus, the use of blocking agents, appropriate adjustments of molar ratios of reactants or a simple manipulation of the order of ligations serve to direct the reactants to form the desired product (i.e., the flanked RNA).

If an mRNA or viral genomic RNA molecule is decapped and 5'-monophosphorylated, treatment with T4 RNA ligase may result in circularizing the RNA molecule since the 3'-hydroxyl terminus of the RNA can function as the acceptor of the donor 5'-phosphoryl terminus of the RNA (Section 5.4.5., infra, explains how to clone a circularized RNA molecule). However, treatment with T4 RNA ligase may also result in forming a long chain of repeating RNA molecules (a concatamer).

In order to prevent circularization or chain formation during ligation reactions one terminus may be blocked by any of several blocking groups which may later be removed; for example, α-methoxyethyl, ethoxymethylidene or photo-labile Q-nitrobenzyl groups may be used as blocking agents. The 3'-terminus of the RNA molecule may be phosphorylated to prevent circularization. Alternatively, an excess of linkers may be added to the reaction to favor the formation of flanked RNA.

Although the ligation reactions may be performed in any order, reaction products may be favored by simply manipulating the order of ligation reactions. For example, (see FIG. 2) capped RNA molecules can function as acceptors but not donors in the T4 RNA ligase reaction. Therefore, a T4 RNA ligase reaction mix containing the capped RNA acceptor and 5'-phosphorylated DNA linkers (which function only as donor molecules) will result in attachment of the DNA linker to the 3'-terminus of the RNA. The possibility of forming concatamers of RNA or circularizing the RNA molecule can be reduced because the capped RNA cannot function as a donor molecule.

Figure 2:
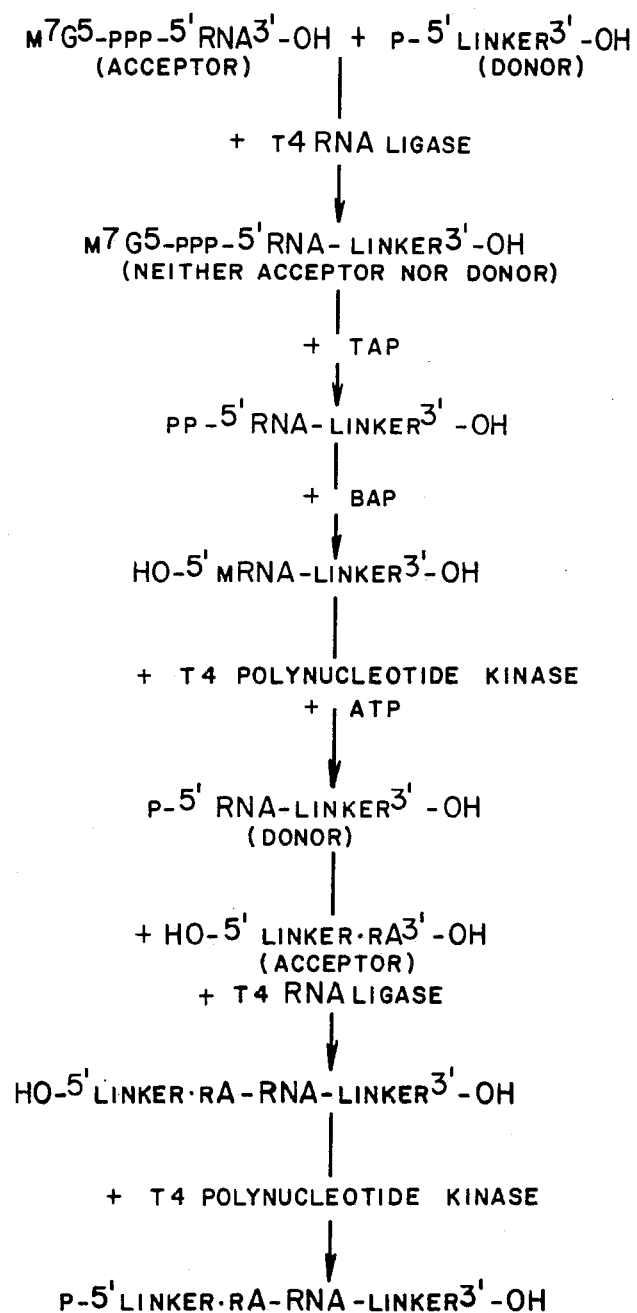
FIG. 2 is a schematic representation of a T4 RNA ligase mediated attachment of DNA linkers to a capped RNA molecule.

Once the DNA linker is ligated to the 3'-terminus of the capped RNA, the molecule functions neither as a donor (because of the cap structure) nor an acceptor (because 3'-hydroxyl terminus DNA molecules are very poor acceptors). After the RNA.DNA molecule is decapped and phosphorylated (e.g., as previously described, using TAP, BAP, followed by T4 polynucleotide kinase plus ATP) the molecule can function as a donor. Then, T4 RNA ligase may be used to mediate the ligation of a mixed DNA-RNA linker which terminates in a 3'-ribonucleotide (e.g., 5'-DNA.rA-3'; or 5'-RNA.DNA.rA-3') to the 5'-terminus of the decapped phosphorylated donor RNA.DNA molecule. In addition, if the mixed DNA-RNA linker molecule has a 5'-hydroxyl terminus, the linker cannot function as a donor, therefore, the linker molecule will not form concatamers; the resulting flanked molecule may be re-phosphorylated after the ligation reaction using T4 polynucleotide kinase plus ATP. Such a scheme (as depicted in FIG. 2) may be used to direct the ligation reactions to favor the formation of desired products without using blocking agents.

5.4. CLONING THE RNA

The linkers which are actually attached to each terminus of the RNA molecule determine the method of cloning and sites for inserting the RNA in an appropriate DNA vector. In fact, cloning the RNA may be accomplished without actually attaching the linkers to the RNA molecule (explained in Section 5.4.5.). The sections which follow (Sections 5.4.1. through 5.4.5.) describe and explain several approaches which may be used in the practice of the present invention. The linker sequences, restriction sites, and plasmid vector used in these sections were chosen merely for the purpose of illustration and are not meant to be limiting. Any appropriate combination of cloning vector and linkers may be used.

5.4.1. CLONING RNA FLANKED BY LINKERS ENCODING RESTRICTION ENZYME SITES

Figure 3:
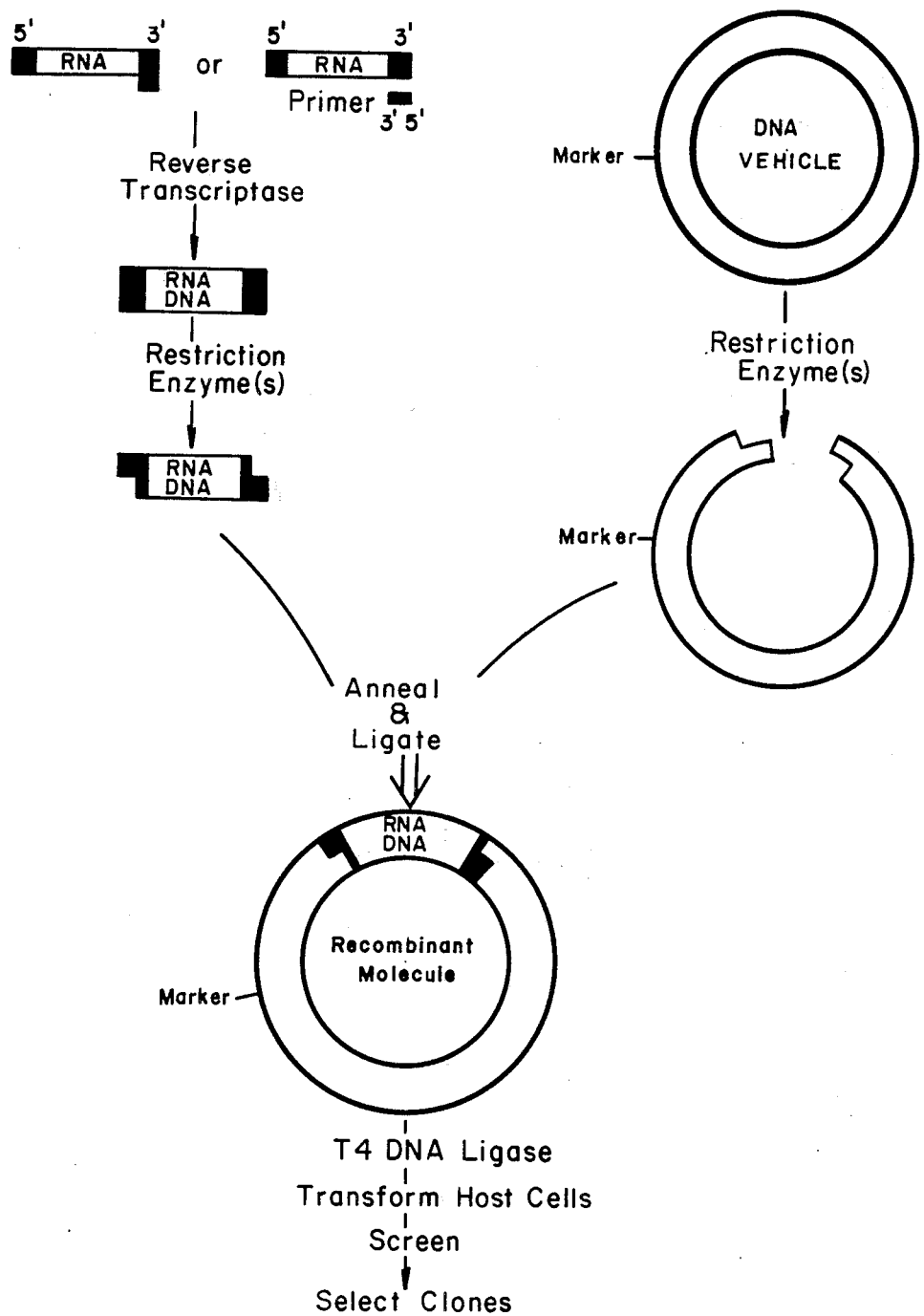
FIG. 3 is a schematic representation of a general method for cloning RNA flanked by oligonucleotide linkers containing sequences of DNA which encode restriction enzyme sites. The linkers at each end may encode restriction sites that yield either 3'-cohesive ends or 5'-cohesive ends.

If the T4 RNA ligase reactions are accomplished so that the RNA is flanked by single-stranded linkers containing DNA sequences which encode specific restriction enzyme cleavage sites, then the flanked RNA molecule can be converted into a double-stranded form so that treatment with the corresponding restriction enzymes will create the cohesive ends necessary for annealing the RNA to a cleaved DNA vector (FIG. 3 depicts the general scheme for this embodiment). A double strand is necessary for this process since most restriction enzymes will not cleave single-stranded molecules.

In order to convert the flanked RNA into a double-stranded molecule, a complementary DNA (cDNA) strand may be synthesized using an RNA-directed DNA polymerase such as reverse transcriptase. The reaction mixture should contain the four deoxyribonucleotides (dG, dC, dA, dT) and may be primed by a single-stranded oligonucleotide consisting of a sequence complementary to the single-stranded linker attached to the 3'-terminus of the mRNA. The resulting double-stranded molecule would then consist of a cDNA/RNA hybrid molecule which is flanked by double-stranded DNA (dsDNA) sequences that code for restriction enzyme cleavage sites. When the hybrid molecule is treated with the site-specific restriction enzymes, the dsDNA flanking sequences are cleaved to form 3' or 5' staggered or cohesive ssDNA ends at each terminus of the hybrid molecule. This flanked hybrid molecule may then be inserted into a cleaved DNA cloning vector which has appropriately-positioned complementary cohesive ends. (N.B., in all approaches described herein, the cleaved vector may also be treated with BAP prior to insertion and ligation of the molecule to be cloned. This prevents the ligation of one cleaved vector to another). After ligation, the resulting recombinant plasmid may be used to transform appropriate host cells.

The presence of the gene sequence as a cDNA/RNA hybrid offers a decided advantage for this process. Most restriction enzymes do not cleave DNA-RNA hybrid molecules; therefore, if one of the flanking restriction sites also occurs within the gene itself, the gene sequence will not be cleaved when the molecule is treated with that particular restriction enzyme. As a result, any appropriate restriction site may be used as a flanking sequence regardless of whether it occurs within the gene sequence itself. However, during cDNA synthesis, a certain amount of second strand synthesis may occur which will convert random segments of the cDNA/RNA hybrid molecule to duplex DNA. If a restriction enzyme recognition sequence is encoded by any of these duplex DNA segments within the cDNA/RNA hybrid molecule, then this site will be sensitive to cleavage by the corresponding restriction enzyme.

An example of this embodiment of the invention is depicted in FIG. 3A. The vector chosen is pBR322 which is cleaved with both EcoRI and BamHI. These are also the two restriction enzyme recognition sites which flank the RNA molecule (EcoRI flanks the 5'-terminus and BamHI flanks the 3'-terminus of the RNA). According to this embodiment of the invention any restriction enzyme recognition sequence may be used for the flanking DNA linkers. Thus both or either of the flanking DNA linkers may be a restriction site which, when cleaved, yields a 3'-staggered (cohesive) end or a 5'-staggered end. The linker sequences may also encode the same site or different sites. Thus, any gene may be tailored for cloning in any desired DNA vector.

5.4.2. CLONING RNA FLANKED BY BOTH SINGLE- AND DOUBLE-STRANDED LINKERS

If the T4 RNA ligase reactions described in Section 5.4.1. are accomplished so that a single-stranded linker (e.g., 5'-ssDNA.rA-3', etc.) is ligated to the 5'-terminus of the decapped 5'-phosphorylated RNA and a double-stranded linker is attached to the 3'-terminus of the RNA (see FIG. 3), then the flanked RNA molecule can be converted to a double-stranded molecule using a DNA polymerase such as reverse transcriptase; however, a primer molecule is not necessary since the complementary strand of the 3'-terminus double-stranded linker serves as a primer for the reverse transcriptase reaction. The subsequent steps for restriction enzyme digestion and insertion into a cloning vector may be accomplished as described in Section 5.4.1.

Figure 3B:
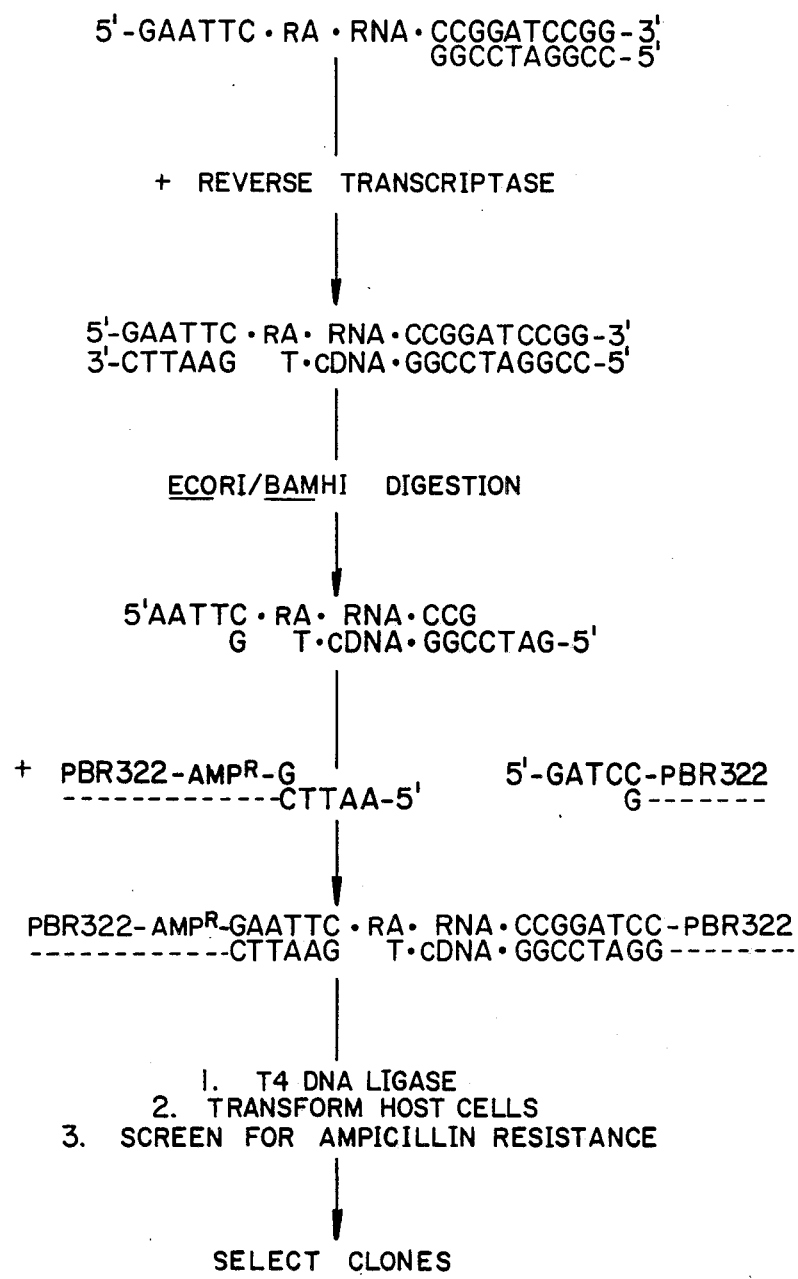
FIG. 3B represents an example of the method of FIG. 2 wherein the RNA, flanked by both single-stranded and double-stranded oligonucleotide linkers, is inserted into the EcoRI and BamHI sites of pBR322.

An example of this process is depicted in FIG. 3B using pBR322 as the vector which is cleaved with EcoRI and BamHI. The RNA is flanked by an ssDNA EcoRI sequence on the 5'-terminus and a dsDNA BamHI sequence at the 3'-terminus.

As explained in Section 5.4.1., the restriction enzyme recognition sequences which make up the flanking DNA linker sequences may be of any type; i.e., the results of digestion can be either 5'- or 3'-staggered (cohesive) ends.

Figure 4:
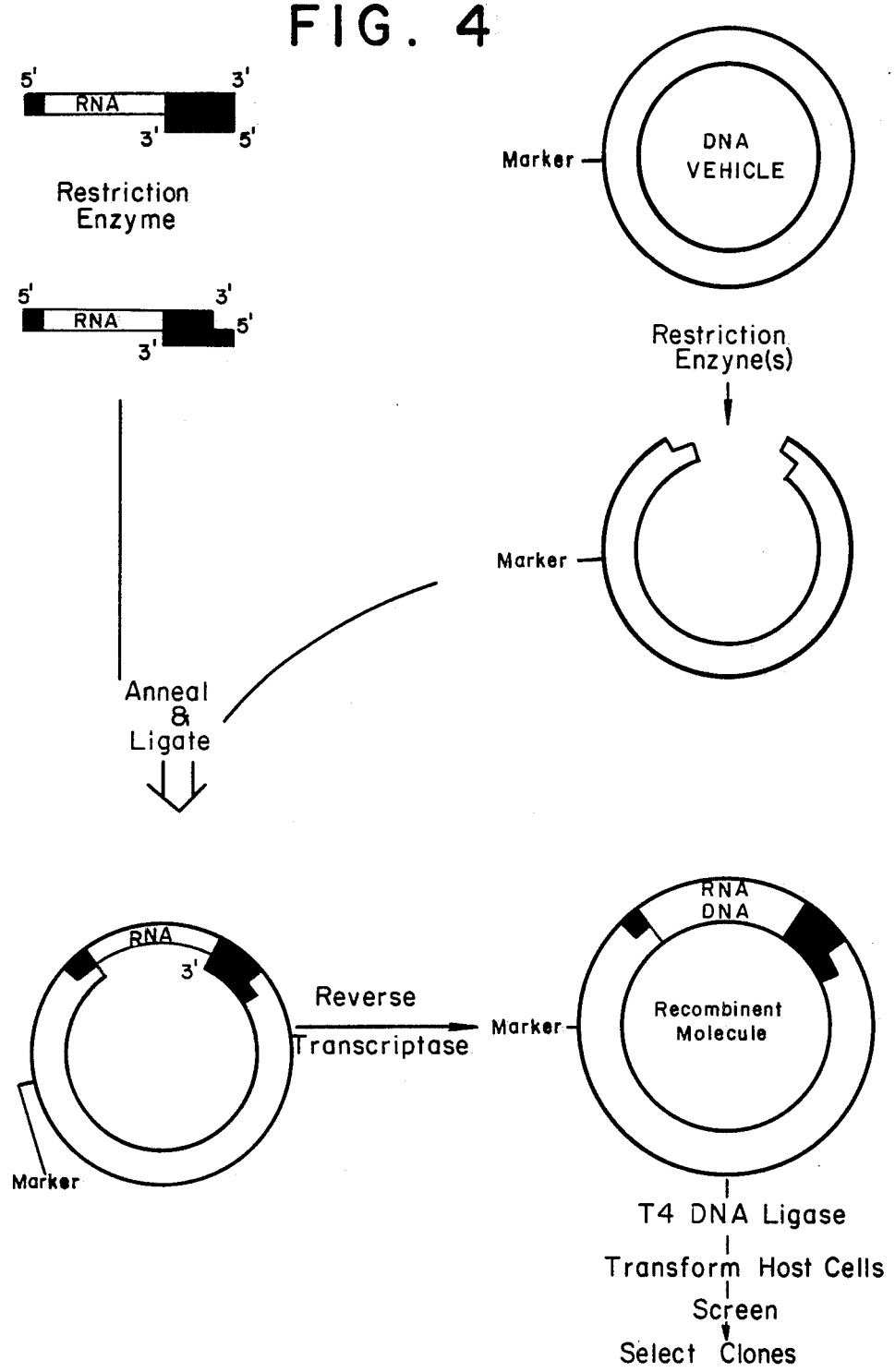
FIG. 4 is a schematic representation of an alternate method for cloning RNA flanked by both single-stranded and double-stranded oligonucleotide linkers. The 5'-terminal single-stranded linker should encode a 5'-cohesive end sequence (or homopolymer); however, the 3'-terminal linker may encode a restriction site that yields either 3'- or 5'-cohesive ends (or homopolymer).

In an alternate embodiment of this procedure (see FIG. 4), the 3'-terminus dsDNA linker may be cleaved by the corresponding restriction enzyme before synthesizing the cDNA strand. Once cleaved, the flanked RNA may be inserted into a cleaved DNA cloning vector having complementary cohesive termini. After the flanked RNA is annealed to the cleaved vector, cDNA synthesis may be accomplished using a DNA polymerase, such as reverse transcriptase. The vector itself serves as a primer for cDNA synthesis. The resultant double-stranded vector may then be ligated using a DNA ligase and used to transform appropriate host cells.

An example of this method is depicted in FIG. 4A, using pBR322 as the vector which is cleaved with the EcoRI and BamHI. The RNA is flanked at its 5'-terminus by a ssDNA.rA linker encoding an EcoRI cohesive end, and at its 3'-terminus by a dsDNA linker encoding a BamHI site.

According to this particular embodiment, the 5'-terminal linker should encode a 5'-cohesive end or a homopolymeric "tail" that is complementary to a 5'-cohesive end or homopolymer generated on a DNA vehicle (N.B., A 5'-homopolymer "tail" may be ligated to a cleaved vector using T4 RNA ligase. Accordingly, the 5'-phosphate of the DNA vector will function as the donor and the homopolymer 3'-hydroxyl will function as the acceptor provided the 3'-terminus of the homopolymer terminates with a ribonucleotide.) However, the 3'-flanking linker may contain DNA sequences that are homopolymers or that encode restriction enzyme recognition sites that yield either 3'- or 5'-staggered termini. In the event that the 3'-terminus linker contains a DNA sequence which encodes restriction site that, upon digestion, yields a 5'-staggered end (as shown in FIG. 4A) then an intervening oligonucleotide sequence in the 3'-flanking linker is necessary to prevent dissociation of the 5'-staggered end from the RNA molecule. The intervening oligonucleotide sequence, depicted as (dN)n and (cN)n in FIG. 4A, should be long enough to prevent dissociation of the cohesive terminus from the flanked single-stranded RNA molecule; thus, the dsDNA intervening sequence could be on the order of 20 nucleotides (i.e., n=20).

5.4.3. CLONING RNA FLANKED BY SINGLE-STRANDED LINKERS

Figure 5:
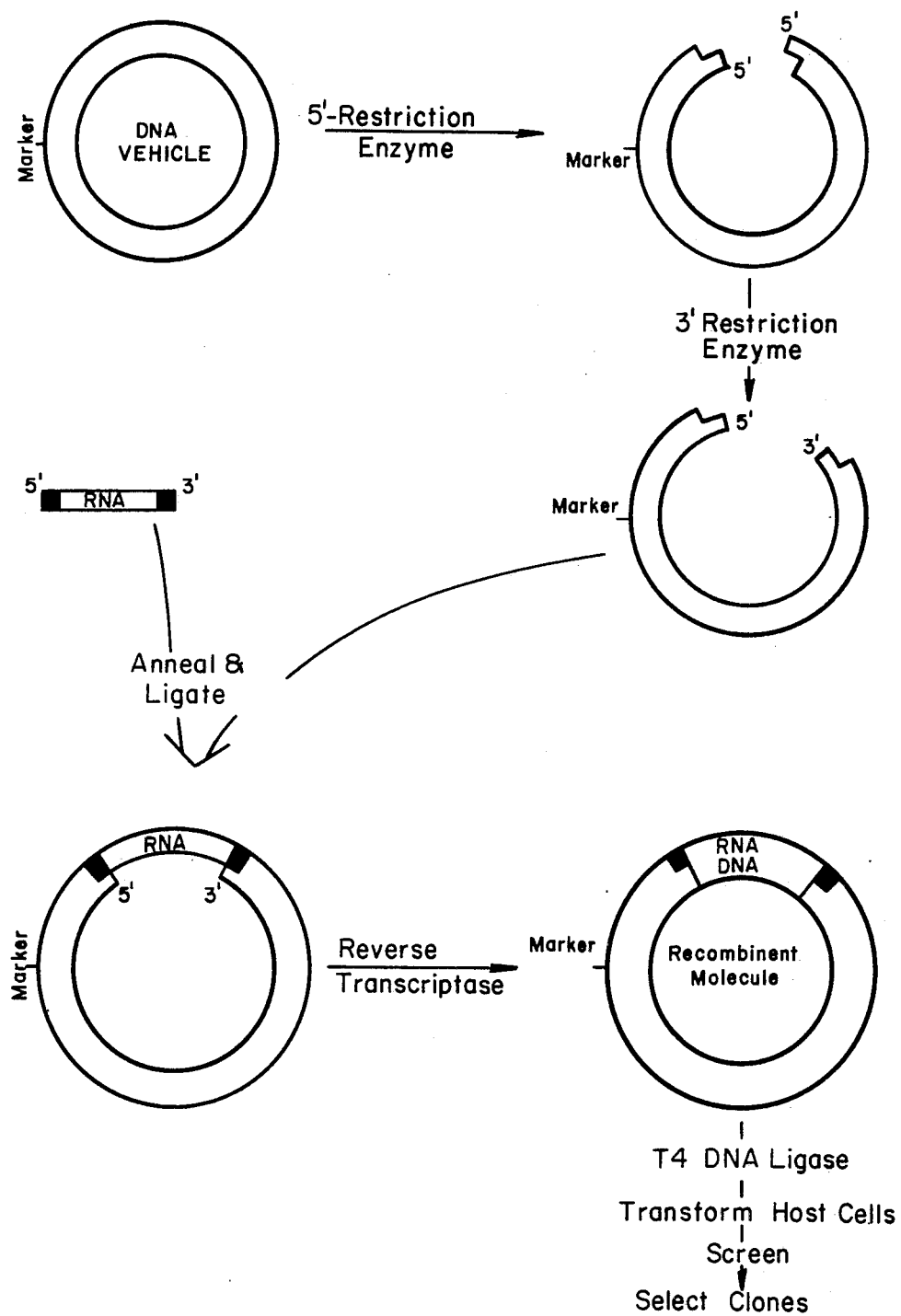
FIG. 5 is a schematic representation of a method for cloning RNA flanked by single-stranded linkers encoding cohesive ends (or homopolymers). In this particular embodiment, the 5'-terminus linker must encode for a 5'-cohesive end (or homopolymer) whereas the 3'-terminus linker must encode a 3'-cohesive end (or homopolymer).

In an alternate embodiment of the invention the RNA molecule may be flanked by single-stranded linkers that code for the staggered cohesive ends of a restriction enzyme site after cleavage (i.e., not necessarily the entire recognition sequence) or homopolymeric "tails". After these linkers are attached to the termini of the RNA molecule via the T4 RNA ligase reaction, the resultant single-stranded oligonucleotide may be directly inserted into a vector which has complementary cohesive ends or complementary homopolymeric 'tails' (see FIG. 5). Then, cDNA synthesis may be accomplished after annealing and ligating the single-stranded flanked RNA to the cleaved vector. The vector itself will serve as a primer for cDNA synthesis using a DNA polymerizing enzyme such as reverse transcriptase. After cDNA synthesis, the recombinant plasmid is ligated and used to transform appropriate host cells.

For the practice of this mode of the invention, the single-stranded linker sequences should be designed to allow annealing and ligation with a cloning vector possessing complementary single-stranded termini. Thus, the single-stranded linker which is attached to the 5'-terminus of the RNA molecule should comprise a sequence that is complementary to a 5'-terminal cohesive end (or homopolymer) which may be generated on the cloning vector. Similarly, the single-stranded linker which is attached to the 3'-terminus of the RNA molecule should be complementary to a 3'-terminal cohesive end (or homopolymer) which may be generated on the cloning vector.

In the preferred practice of this embodiment of the invention, the single-stranded linkers should comprise DNA (e.g., DNA.rA at the 5'-terminus; DNA or RNA.DNA at the 3'-terminus) so that ligation of the flanked molecule to the vector may be easily accomplished using T4 DNA ligase. However, if the 5'-terminus is flanked with a ssDNA.rA linker and the 3'-terminus is flanked with an RNA linker then the 5'-terminus of the flanked RNA molecule may be ligated to the vector using T4 DNA ligase, whereas the 3'-terminus of the flanked RNA molecule may be ligated to the vector using T4 RNA ligase.

Figure 5A:
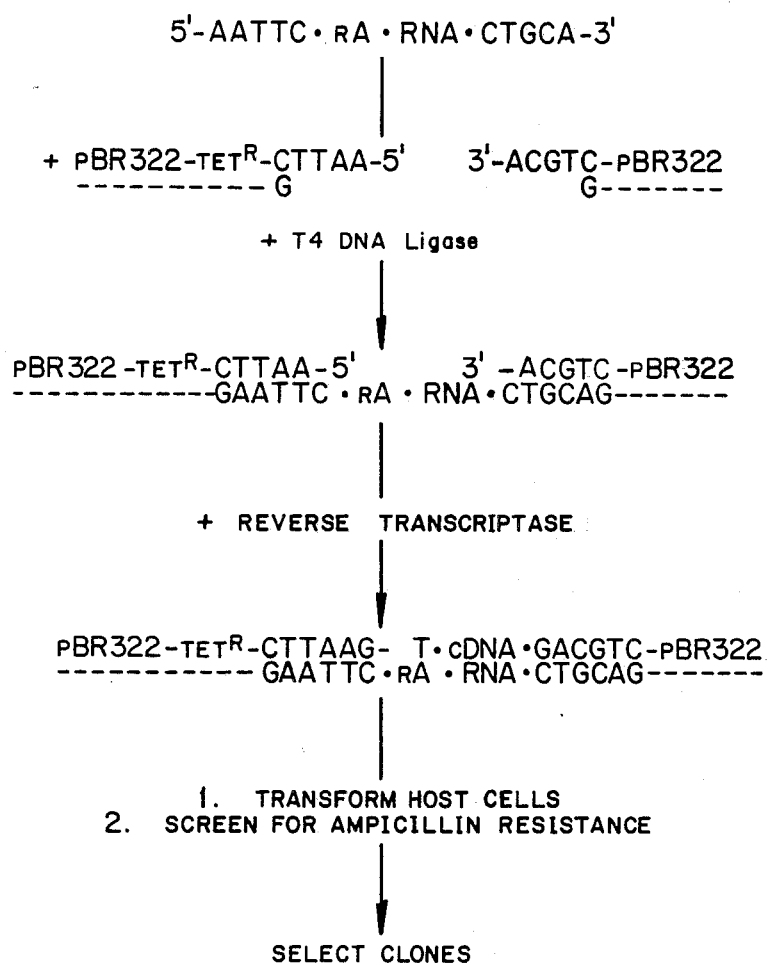
FIG. 5A represents an example of the method of FIG. 4, wherein the RNA is inserted into the EcoRI and PstI sites of pBR322.

FIG. 5A, depicts an example of this embodiment wherein a ssDNA.rA linker comprising an EcoRI cohesive end sequence is attached to the 5'-terminus of an RNA molecule; whereas a ssDNA linker comprising a PstI sequence flanks the 3'-terminus of the RNA. These sequences are complementary to the 5'-cohesive end of the EcoRI site and the 3'-cohesive end of PstI site located on the cleaved plasmid, pBR322. The vector and restriction sites used in FIG. 5A are merely illustrative and any combination of 5'- and 3'-staggered end restriction sites may be used with any appropriate vector in the practice of the present invention.

5.4.4. CLONING RNA POSSESSING A 5'-TERMINUS SINGLE-STRANDED LINKER

Figure 6:
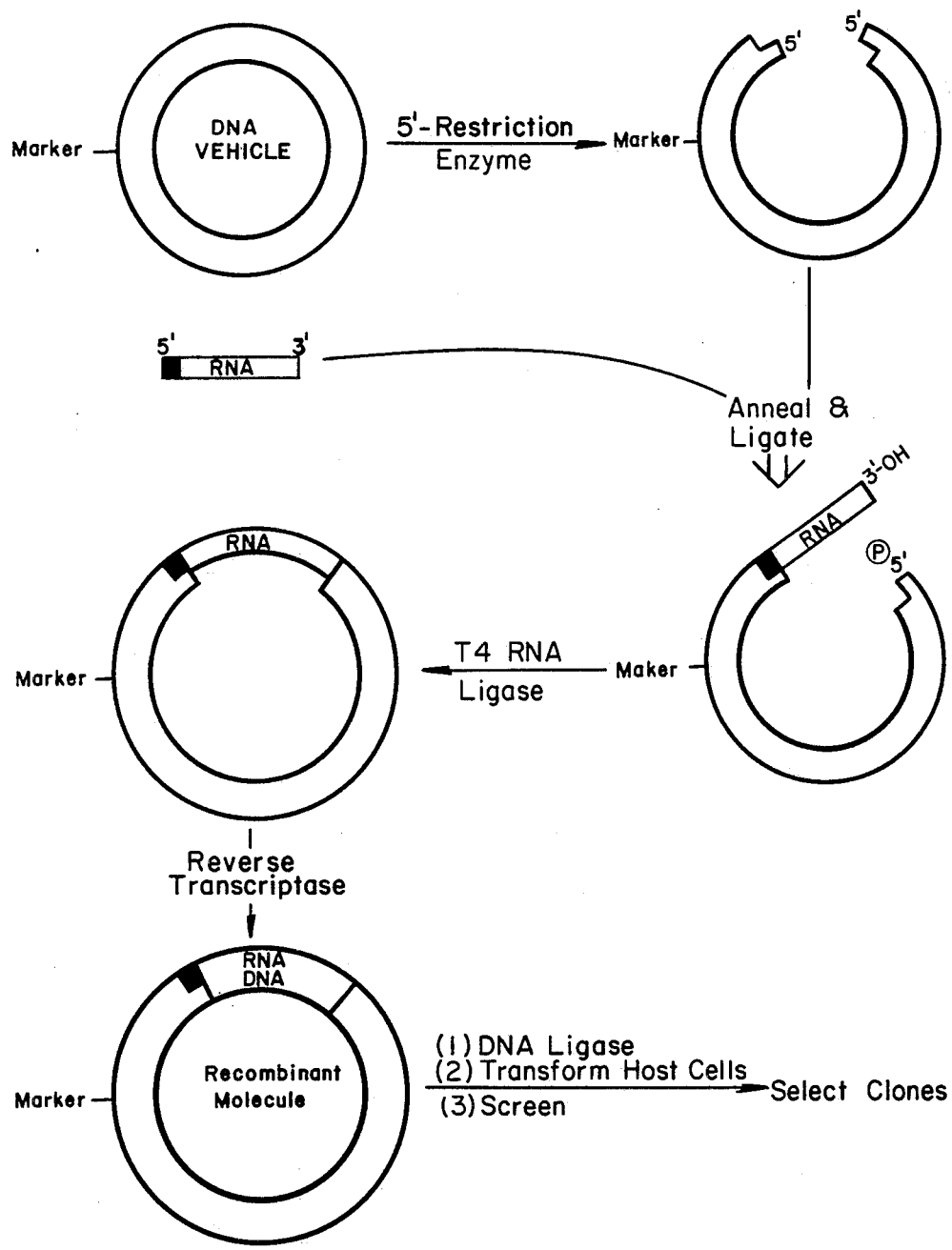
FIG. 6 is a schematic representation of a method for cloning RNA flanked by a single-stranded oligonucleotide liner at the 5'-terminus only. In this instance, the 5'-terminus linker must encode for a 5'-cohesive end (or homopolymer).

According to another embodiment of the present invention, RNA which is flanked by a single-stranded linker (e.g., DNA.rA or DNA.RNA) at the 5'-terminus may be cloned in a DNA vector without attaching a linker to the 3'-terminus of the RNA molecules (see FIG. 6). The 5'-terminus linker sequence should be complementary to a restriction enzyme 5'-cohesive end (or homopolymer) generated on a cleaved DNA cloning vector. After base-pair hybridization and ligation, T4 RNA ligase may be used to ligate the 3'-hydroxyl terminus of the RNA to the opposite 5'-phosphoryl terminus of the DNA vector. In this T4 RNA ligase reaction, the 3'-hydroxyl RNA functions as the acceptor molecule and the 5'-phosphate DNA vector functions as the donor molecule.

After ligation with T4 RNA ligase, the cDNA strand may be synthesized by using a DNA polymerase such as reverse transcriptase. The vector itself serves as the primer for the cDNA synthesis. The resultant recombinant vector may then be ligated using T4 DNA ligase and used to transform appropriate host cells.

Figure 6A:
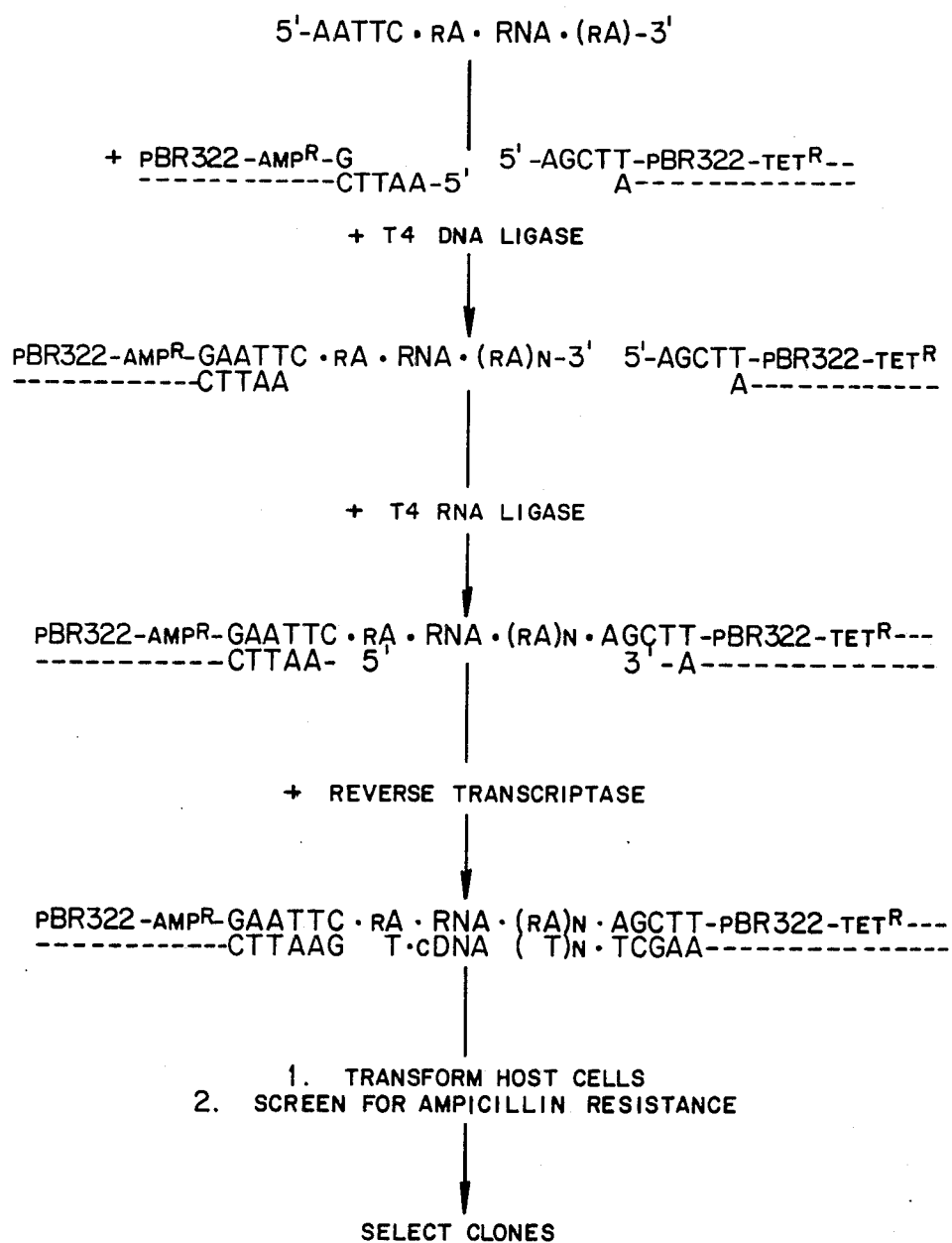
FIG. 6A represents an example of the method of FIG. 5 wherein the RNA is polyadenylated and inserted into the EcoRI and HindIII sites of pBR322.

An example of this embodiment is depicted in FIG. 6A wherein the RNA molecule possesses a 3'-poly(A) tail and is flanked on its 5'-terminus by ssDNA.rA linker sequence which comprises an EcoRI 5'-cohesive end. This is ligated (e.g., using T4 DNA ligase) to pBR322 which was cleaved with EcoRI and HindIII. The 3'-hydroxyl terminus (poly(A) tail) of the RNA is ligated to the 5'-staggered end of the HindIII site on the vector (5'-AGCTT-pBR322) using T4 RNA ligase: thus, the full HindIII sequence is restored (5'-AAGCTT-3'). For the practice of this embodiment of the invention the 5' linker may encode any 5'-cohesive end or homopolymer which is complementary to any suitable restriction site or homopolymer generated on the vector.

In order to effect the T4 RNA ligase mediated ligation of the 3'-hydroxyl terminus of the RNA molecule to the DNA vector, the vector can be cleaved with a restriction enzyme that results in either a 5'-cohesive terminus or a blunt terminus (because both single-stranded and double-stranded DNA molecules are suitable donors in the T4 RNA ligase reaction). Thus, cleavage of the vector at one restriction site which results in 5'-cohesive ends is all that is necessary for the practice of this mode of the invention. However, two or more restriction sites on the vector may be cleaved as desired for insertion of the RNA.

When the RNA molecule terminates with rA or has a 3'-poly(A) tail (e.g., certain mRNAs or any RNA molecule treated with poly(A) polymerase) an additional advantage is obtained if the vector cleavage site is a restriction enzyme recognition sequence which commences with adenylic acid, (for example, HindIII, BglII, HsuI to name a few), since ligation of the 3'-terminus poly(A) tail of the RNA restores the restriction enzyme site by replacing the initial adenylic acid (see FIG. 6A). However, if the first nucleotide of the restriction sequence is a dT (e.g., XbaI, BclI, or TagI, etc.), dC (e.g., HpaII, XmaIII, BluI, XhoI, AvaI, etc.), or dG (e.g., EcoRI, HinfI, BamHI, etc.) then the restriction site is not restored after T4 RNA ligation of a polyadenylated RNA molecule to the vector. Instead, the restriction site is destroyed by the replacement of the first nucleotide in the restriction site recognition sequence with the 3'-terminal rA of the polyadenylated RNA molecule.

Destruction of the restriction sites beginning with dT, dC or dG may be avoided if the polyadenylated RNA molecule (or any RNA molecule) is modified prior to ligation by attaching the appropriate ribonucleotide to the 3'-terminus of the RNA. This attachment may be accomplished via a T4 RNA ligase mediated reaction. A short oligoribonucleotide chain of oligo(T), oligo(C), or oligo(G) may be ligated to the 3'-terminus of the RNA molecule using T4 RNA ligase. Therefore, any RNA molecule may be so modified to possess a short oligoribonucleotide chain consisting of the ribonucleotide which will result in restoration of the restriction site.

Figure 6B:
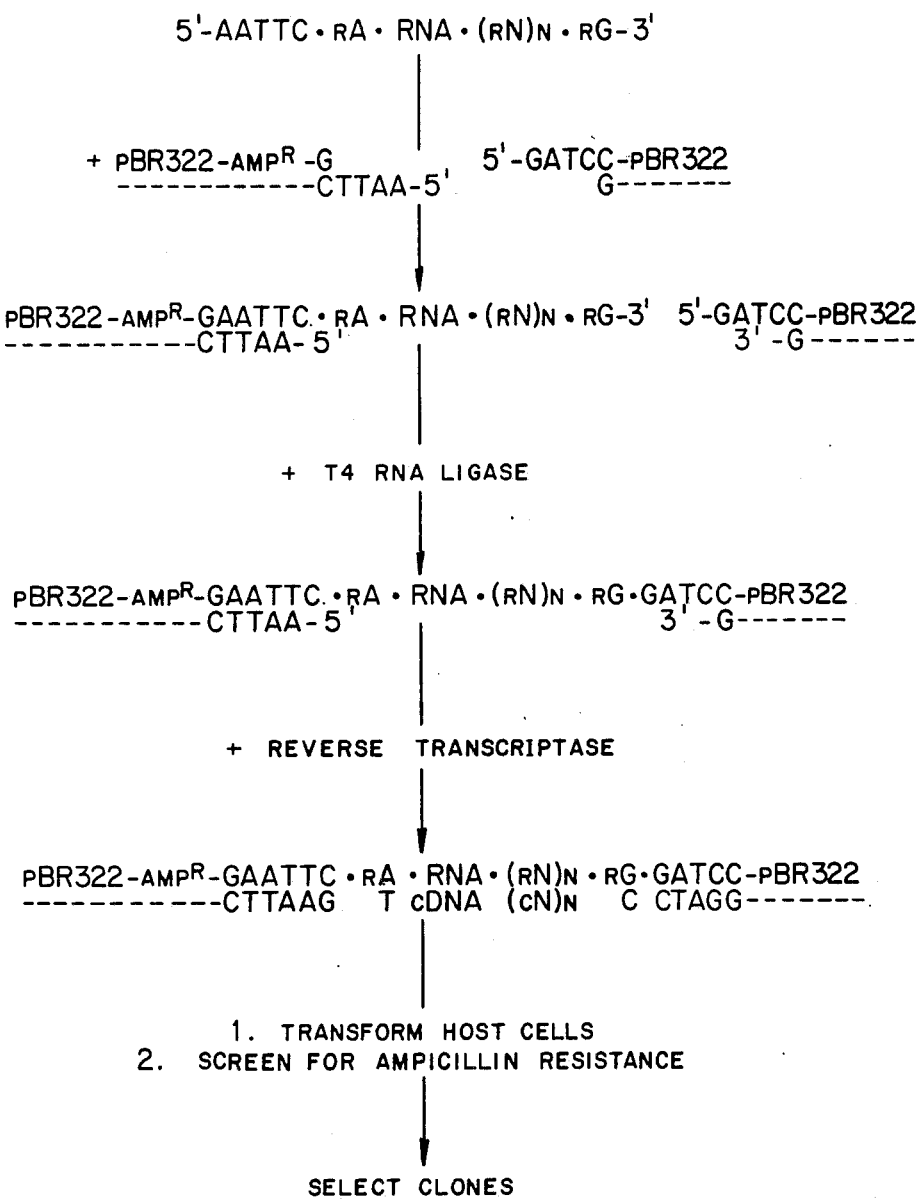
FIG. 6B represents another example of the method of FIG. 5 wherein the 3'-terminus of the RNA is flanked by an appropriate oligoribonucleotide linker. This results in restoration of the restriction site in the recombinant vector.

Attachment of ribonucleotides to the 3'-terminus of RNA may be accomplished before or after ligation of the ssDNA/RNA linker to the RNA 5'-terminus. An example of the process for cloning the modified RNA prepared as described herein is depicted in FIG. 6B. The RNA molecule in FIG. 5B contains a 5'-ssDNA.rA linker coding for an EcoRI cohesive end; whereas the 3'-terminus of the RNA molecule is modified by the addition of a terminal rG. The T4 RNA ligase attachment of the RNA 3'-terminal rG to the cleaved BamHI site on pBR322 restores the BamHI restriction site. In FIG. 6B, (N)n represents oligo(G), oligo(T), oligo(C), or oligo(A). If n=1 then (N)n may be pAp, pTp, pCp, or pGp (in the case of pGp the terminal rG is not required).

5.4.5. CLONING RNA BY CIRCULARIZATION

This embodiment of the present invention allows cloning of an RNA molecule with or without oligonucleotide linkers attached. The general scheme is diagrammatically represented in FIGS. 7 and 7A.

Mixed linkers (i.e., linkers composed of DNA, RNA, or a mixture of each) which contain DNA encoding any restriction enzyme recognition site may be attached (as previously described in Section 5.3.) to either or both termini of the RNA molecule to be cloned (see FIG. 7). While the restriction enzyme recognition site of the linker(s) should be encoded by DNA, for the practice of this particular embodiment the 3'-terminal nucleotide of the linker(s) should be a ribonucleotide. Of course, when two linkers are utlilized the linkers may encode the same or different restriction sites. (N.B., the use of the different restriction sites will ultimately allow the directional insertion of the RNA molecule into a DNA cloning vector).

When an RNA molecule is treated with T4 RNA ligase, the 3'-hydroxl group of the 3'-terminal ribonucleotide can function as an acceptor for the 5'-terminal phosphoryl group; as a result, the RNA molecule will be ligated to form a circle (see FIG. 7).

The circular RNA molecule may then be used as a template for cDNA synthesis which can be accomplished using an RNA directed DNA polymerase such as reverse transcriptase in the presence of the four deoxyribonucleotides and any appropriate primer. Preferably the primer molecule should be a DNA sequence that is complementary to the linker sequence which was previously attached to the RNA molecule. Synthesis of cDNA will result in a circular double-stranded cDNA/RNA hybrid molecule which possesses a dsDNA restriction enzyme recognition site. (N.B., due to the RNase H activity of reverse transcriptase, random portions of the circular RNA template will be removed during cDNA synthesis and replaced with DNA. This limited second strand synthesis will result in a number of duplex DNA sites interspersed throughout the circular hybrid molecule.)

After cDNA synthesis, the DNA should be ligated (e.g., using T4 DNA ligase) and the circular hybrid molecule may then be cleaved at the duplex DNA restriction enzyme site using the appropriate restriction enzyme. Finally, the cDNA/RNA hybrid molecule which now possesses cohesive termini can be annealed and ligated to a DNA cloning vector which possesses complementary cohesive ends. The resulting recombinant molecules are then used to transform host cells, which during growth and replication will produce multiple DNA copies of the recombinant vector.

FIG. 7A diagrammatically demonstrates how the circularization process can be used to clone an RNA molecule which is not flanked by linkers. The mRNA molecule should be prepared for T4 RNA ligase mediated reactions as previously described (e.g., the RNA molecule should be decapped, dephosphorylated, rephosphorylated, and de-proteinated if necessary). When a properly prepared RNA molecule is treated with T4 RNA ligase the 3'-hydroxyl group will function as an acceptor and the 5'-phosphoryl group will function as a donor resulting in a circular RNA molecule.

After circularization, cDNA synthesis may be accomplished using reverse transcriptase and an appropriate primer (N.B., if the RNA species to be cloned is polyadenylated, then an oligo (dT) primer may be used; however, when using non-polyadenylated RNA species a certain amount of sequence data may be required in order to select or synthesize a primer which is complementary to some portion of the RNA molecule). As previously explained, a certain degree of second strand synthesis will occur during the reverse transcriptase reaction. As a result, the circular RNA template is converted to a circular cDNA/RNA hybrid containing duplex DNA interspersed throughout the molecule. If one of the duplex DNA sites encodes a restriction enzyme recognition sequence, then the circular cDNA/RNA hybrid may be cleaved at that site using the corresponding restriction enzyme. The cleaved hybrid molecule may then be inserted into a DNA cloning vector having complementary cohesive ends.

Alternatively, the cDNA/RNA hybrid molecule may be ligated using T4 DNA ligase, the hybrid molecule may be treated with alkali or RNase in order to remove the RNA template. The resulting single-stranded circular cDNA molecule may be treated with a DNA polymerizing enzyme in the presence of the four deoxyribonucleotides and an appropriate primer in order to polymerize the second strand (using the cDNA as template) and convert the molecule to a duplex circular DNA. (N.B., after the removal of the RNA species from the cDNA/RNA hybrid molecule, the pieces of DNA which were synthesized via the limited second-strand synthesis that occurred during cDNA synthesis will function as primers for the synthesis of the second strand). The duplex DNA molecule may now be ligated and treated with appropriate restriction enzymes (one or more) to generate cohesive ends that are complementary to those of any cloning vector (N.B., this requires a knowledge of at least one restriction site within the molecule to be cloned). Once annealed and ligated, the recombinant vector is used to transform appropriate host cells which will generate multiple DNA copies of the recombinant molecule during replication and growth.

It should be noted that it is entirely possible that the circularization phenomena described above may occur in the practice of *any* of the foregoing methods discussed in Sections 5.4.1 through 5.4.4. (i.e., during ligation of the linkers to an RNA molecule to be cloned, a number of RNAs will circularize with or without successful linker attachment). Thus, the techniques disclosed herein will enable the successful cloning of RNA, however, in practice, a variety of reaction mechanisms are possible and may occur within the same reaction vessel.

5.4.6. ALTERNATE METHOD FOR CLONING POLYADENYLATED RNA

This embodiment of the present invention, which is diagrammatically represented in FIG. 8, comprises cleaving any DNA cloning vector with a restriction enzyme that generates cohesive ends (3'or 5') or blunt ends. The cleaved vector may then be tailed with ribonucleotides using the enzyme terminal deoxynucleotidyl transferase (TdT). The enzyme, TdT, catalyzes the polymerization of deoxyribonucleotide triphosphates at the 3'-termini of double-stranded or single-stranded DNA molecules and is used in homopolymeric tailing reactions; TdT also catalyzes a limited addition of the four ribonucleoside triphosphates to the 3'-hydroxyl termini of DNA (i.e., ribonucleotide tails would be approximately three nucleotides long). Once the vector is tailed with ribonucleotides (in FIG. 8 denoted as rNrNrN) it is then cleaved at a second restriction site in order to remove one ribonucleotide tail and generate a 5'-terminal cohesive end. Subsequently, an oligonucleotide linker which is complementary to the 5'-cohesive end and has a 3'-oligo (dT) homopolymeric tail is annealed and ligated to the vector. The vector now possesses a 3'-homopolymeric DNA tail (in FIG. 8 denoted as $(dT)_{16}$) and a 3'-homopolymeric RNA tail (in FIG. 8 denoted as rNrNrN).

The vector thus prepared is then annealed to a polyadenylated RNA molecule which has been properly decapped, phosphorylated, de-proteinated, etc., as previously described. Any polyadenylated RNA species may be used, e.g., mRNA, certain viral RNA molecules, etc.; in fact, poly(A) chains can be added to poly-(A)-minus RNA preparations using the enzyme poly(A) polymerase. Poly(A) polymerase polymerizes the AMP of ATP onto the free, 3'-terminal hydroxyl group of RNA. The polymerase reaction will also incorporate CTP and UTP into RNA but to a far lesser extent.

After the polyadenylated RNA molecule anneals to the prepared vector via base-pair hybridization of the RNA poly(A) tail and the DNA $(dT)_{16}$, ligation is accomplished using T4 RNA ligase (as a result the 3'-hydroxyl group of the vector homopolymeric RNA tail (rNrNrN) is the acceptor of the 5'-phosphate of the RNA molecule; furthermore the 3'-hydroxyl of the RNA poly(A) tail is the acceptor of the 5'-phosphate generated on the DNA vector itself). Then an RNA directed DNA polymerase, e.g., reverse transcriptase, is used to synthesize the second strand. The resulting recombinant molecule may be ligated using T4 DNA ligase and used to transform appropriate host cells which will generate multiple DNA copies of the recombinant molecule.

It should be noted that this embodiment is not limited to using a polyadenylated RNA. T4 RNA ligase can be used to attach any homopolymer to the 3'-hydroxyl of any RNA molecule. Of course, the vector should be modified as previously described to possess the complementary homopolymer.

6. EXAMPLE: MOLECULAR CLONING OF B-GLOBIN mRNA

The following examples demonstrate one method of the invention for cloning β-globin mRNA in a DNA vector which is a pBR322 derivative.

6.1 SYNTHESIS OF LINKERS FOR ATTACHMENT TO mRNA TERMINI

Synthesis of linkers for use in the following examples was accomplished using the Kempe technique (described in Section 5.1.) as follows:

A. Syntheis of Oligoribonucleotides on Silica as Solid Support.

Oligoribonucleotides were synthesized by solid phase chemistry using the 2'-benzoylated 5'-DMTr base protected ribonucleosides phosphoamidites prepared as described in Section 5.1. (and depicted in FIG. 1). The steps in the automated solid phase synthesis are shown in the Unit File (Table I). Synthesis of oligoribonucleotides on silica solid support have also been reported by Ogilvie and Nemer, (1980, Tetrahedron Lett.: 4159) using methylchlorophosphite reagents of the 2'-silylated ribonucleosides.

TABLE I

A Unit File: Steps in Automated Synthesis on 200 mg of Functionalized Silica

| Steps | Minutes | Valves (Reagents, 2 ml/min) |
|---|---|---|
| 1 | 10 | DT[a] |
| 2 | 5 | THF |
| 3 | .2 | MIX[b] |
| 4 | .2 | U[c] |
| 5 | .1 | MIX |
| 6 | .1 | U |
| 7 | .1 | MIX |
| 8 | .1 | U |
| 9 | .1 | MIX |
| 10 | .2 | U |
| 11 | .2 | MIX |
| 12 | 5 | RE[d] |
| 13 | 4 | THF |
| 14 | .2 | RE |
| 15 | 3 | OX[e] |
| 16 | 3 | THF |
| 17 | 2 | CAP[f] |
| 18 | 3.5 | RE |
| 19 | 3.5 | THF |
| 20 | .2 | RE |

[a]detritylating reagent: 70 g $ZnBr_2$ in 500 ml $CH_3NO_2$ and 1% $H_2O$.
[b]activation reagent for phosphoamidite: 2.1 g 1H-tetrazole in 120 ml $CH_3CN$.
[c]nucleotide: 1 mMol in 20 ml $CH_3CN$.
[d]recycling valve: is closed when extensive reaction time is required and when void volume has to be washed out.
[e]oxidizing reagent: 1 g $I_2$ in 250 ml THF, 120 ml $H_2O$ and 25 ml 2,6-lutidine.
[f]capping reagent: Solution A:B, 1:1, v/v; solution A: 100 ml sym-collidine, 80 ml $Ac_2O$ and 400 ml THF; solution B: 25 g N—dimethylaminopyridine in 500 ml THF.

The RNA species which were prepared are listed in Table II. Each nucleotide coupling proceeded in 85–95% yield as measured by the dimethoxytrityl cation absorption at 470 nm in a flow-thru visible UV-cell. After the solid phase synthsis was complete, the oligoribonucleotide attached to the support was deprotected at the phosphotriester with thiophenoxide for 1.5 hours and then removed from the support by treatment with concentrated ammonia for 1 hour at room temperature. The ammonia solution was then heated at 50° C. for 4 hours to complete the deprotection of the nucleotide bases. The aqueous ammonia solution was separated from the support by filtration and the sample was evaporated to dryness.

Since prolonged treatment of RNA with ammonia resulted in internucleotide cleavage, reaction conditions were sought in which decomposition was minimized under conditions for removal of benzoyl and isobutyryl protecting groups from the purine and pyrimidine bases. The compound for the study was $rA_{10}$ which was commercially available (Boerhinger-Mannheim). As seen in Table III, ammonolysis completely cleaved the model compound rA$_{10}$ within a few hours at 50° C. A drastically reduced internucleotide cleavage was obtained in a mixture of n-butylamine-methanol-dioxane (1:1:2, v/v) which removed N-benzoyl groups within 3–7 hours at 40° C. Those RNA which were synthesized and separated from the silica support were thus treated with the milder butylamine reagent for deprotection of the bases. Oligomers containing G$^{Bz}$ were treated with the butylamine reagent for 7 hours and the ones with G$^{iBu}$ for 5 hours. After the reaction was completed, the mixture was evaporated and the residue taken up in water. The resultant dimethoxytritylated oligoribonucleotides were purified on HPLC with acetonitrile in 0.1 M triethylammonium acetate. The isolated, tritylated compounds were treated with 80% acetic acid-water for 10 minutes, the acid was removed by evaporation under reduced pressure and the residue was taken up in water for purification by HPLC as the fully deprotected oligoribonucleotide. The synthetic RNA were converted to 5'-[$^{32}$P]- labeled compounds and treated with snake venom phosphodiesterase. The partially digested mixtures were characterized by the methods of 2-dimensional electrophoresis and homochromatogaraphy. Two of the oligoribonucleotides that were prepared, rU$_6$ and rA$_{10}$, could be compared with authentic samples (Boerhinger-Mannheim); they proved to be identical under analyses by HPLC and homochromatography.

file in Table I. The 5'-0-(dimethoxytrityl)deoxynucleoside-3'- (N,N-dimethylamino-methoxy)phosphine were prepared in the same manner as the amidites of ribonucleosides. A list of the mixed DNA-RNA prepared in this manner is given in Table II along with the HPLC isolation conditions. The compounds d(GAT)r(CCC) and r(GGG)d(CATG) were also prepared from the 2'-trimethoxybenzoylated ribonucleosides. Analysis by 2-dimensional electrophoresis and homochromatography was also performed.

6.1.1. SYNTHESIS OF LINKERS FOR ATTACHMENT TO THE 5'-TERMINUS OF THE mRNA MOLECULE

The DNA portion of the linker which was synthesized for attachment to the 5'-terminus of the mRNA molecule was eight deoxyribonucleotides long and encoded the EcoRI restriction site as follows:

In order to attach this synthetic ssDNA sequence to the 5'-terminus of an RNA molecule, via a T4 RNA ligase reaction, the linker was synthesized to contain a 3'-terminus ribonucleotide, adenylic acid (rA); thus the sequence of the synthetic linker for attachment to the 5'-terminus of the mRNA molecule was:

TABLE II

| | HPLC Separation and Yields of Oligonucleotides of RNA and mixed DNA-RNA | | |
|---|---|---|---|
| Oligonucleotides | Gradient over 30 min of CH$_3$CN (%)/0.1 M Et$_3$NH$^+$OAc$^-$ | R$_t$ (min) | O.D.$_{260}$ (% yield)$^c$ |
| DMTr-rU$_6$ | 25–35%, a | 21 | 70 (6.3%) |
| rU$_6$ | 10–20%, b | 7 | 45 (4.0%) |
| DMTr-rA$_{10}$ | 20–30%, a | 27 | 55 (3.7%) |
| rA$_{10}$ | 8–18%, b | 25 | 36 (2.4%) |
| DMTr-r(AAUUCUAGAUCU) | 20–30%, b | 17 | 65 (2.0%) |
| r(AAUUCUAGAUCU) | 10–20%, b | 12 | 34 (1.0%) |
| DMTR-d(GAT)r(CCC) | 25–35%, a | 15 | 88 (5.9%) |
| d(GAT)r(CCC) | 8–18%, a | 13 | 50 (3.4%) |
| DMTr-r(GGG)d(CATG) | 20–30%, a | 24 | 71 (5.4%) |
| r(GGG)d(CATG) | 10–20%, b | 16 | 45 (3.4%) |
| DMTr-d(CCGAATTC)rA | 20–30%, b | 22 | 120 (12.6%) |
| d(CCGAATTC)rA | 10–20%, b | 18 | 88 (9.2%) |
| DMTr-r(UUU)d(CCGAATTC)rA | 20–30%, b | 18 | 115 (9.7%) |
| r(UUU)d(CCGAATTC)rA | 10–20%, b | 15 | 85 (7.2%) |
| DMTr-d(GAAA)r(UU)dGr(UU)dArUd(CC) | 20–30%, a | 23 | 75 (3.6%) |
| d(GAAA)r(UU)dGr(UU)dArUd(CC) | 10–20%, a | 22 | 51 (2.4%) | a. Altex Ultrasphere ODS, 5μ semiprep column, flow = 3 ml/min.
b. Altex Ultrasphere ODS, 5μ analytical column, flow = 1 ml/min.
c. Isolated from 200 mg of functionalized silica.

TABLE III

| | Deprotection of Purines and Internucleotide Cleavage | | | |
|---|---|---|---|---|
| | Treatment with conc. NH$_3$ at 50° C. | | Treatment with nBuNH$_2$—MeOH—dioxane (1:1:2, v/v) at 40° C. | |
| Base protected ribonucleoside | reaction time$^a$ | decomposition$^b$ of rA$_{10}$ | reaction time$^{a,c}$ | decomposition$^{b,d}$ of rA$_{10}$ |
| rA$^{Bz}$ | 2 h | 93% | 3 h | 7% |
| rG$^{iBu}$ | 4 h | 98% | 5 h | 12% |
| rG$^{Bz}$ | 5 h | 100% | 7 h | 17% |

$^a$greater than 95% deprotection; extent of deprotection monitored by analytical TLC, silica gel, 20% MeOH/CH$_2$Cl$_2$.
$^b$Decomposition from internucleotide cleavage determined by analysis on reversed phase HPLC.
$^c$The same result was obtained in a study of the DMTr-ribonuclosides (analysis on TLC, silica gel, 10% MeOH/CH$_2$Cl$_2$).
$^d$The amount of decomposition corresponding to the length of reaction time was obtained from a linear plot of residual rA$_{10}$ vs. time.

B. Mixed DNA-RNA Synthesis.

The introduction of the 2'-benzoate as a protecting group for ribonucleotides in solid phase synthesis allowed the synthesis of any combination of DNA-RNA. The mixed DNA-RNA were synthesized using the unit

6.1.2. MODIFICATION OF ssDNA LINKERS FOR ATTACHMENT TO THE 3'-TERMINUS OF THE mRNA MOLECULE

The ssDNA linker which was synthesized for attachment to the 3'-terminus of the mRNA molecule was twelve deoxribonucleotides in length and coded for the BamHI and EcoRI restriction sites as follows:

5'-dGdGdAdTdCdCdGdAdAdTdTdC-3'

In order to attach this synthetic ssDNA sequence to the 3'terminus of an RNA molecule, via a T4 RNA ligase reaction, the linker was modified by phosphorylating the 5'-terminus using T4 polynucleotide kinase.

The enzyme, T4 polynucleotide kinase catalyzes the transfer of the γ-phosphate group of ATP to the 5'-hydroxyl terminus of a DNA or RNA molecule. The activity requirements for the enzyme include $Mg^{++}$ as a cofactor and dithiothreitol (DTT) as the reducing agent (Maxam and Gilbert, 1977, Proc. Natl. Acad. Sci., U.S.A. 74: 560). One unit of enzyme (P.L. Biochemicals, Milwaukee, Wis.) catalyzes the transfer of 1nmol phosphate to the 5'-OH end of a polynucleotide from $[\gamma-^{32}P]$-ATP in 30 minutes at 37° C.

Approximately 1 μg of DNA linker was added to 15 μl Kinase Buffer which consisted of: 0.05M Tris.HCl (pH 7.5), 0.01M $MgCl_2$, 0.001M DTT and 0.2–0.5 units T4 polynucleotide kinase. The reaction mixture was incubated at 37° C. for 30 minutes and stopped by heating to 65° C. for 5 minutes. The heat treatment inactivates the T4 polynucleotide kinase so that the entire mixture containing the 5'-phosphorylated linker may be added directly into a reaction mixture for T4 RNA ligase mediated joining of the 5'-terminus of the DNA linker to the 3'-terminus of the B-globin mRNA.

6.2. ISOLATION OF B-GLOBIN mRNA

For the purposes of the examples, the globin mRNA was isolated from rabbit reticulocytes. The preparation of rabbit reticulocytes was essentially as described (Villa-Komaroff, et al., 1974, Methods in Enzymology 30: 709). New Zealand White Rabbits (4–6 pounds) were made anemic by daily subcutaneous injections of 1.2% acetyl phenylhydrazine (neutralized to pH 7.5 with 1M Hepes, pH 7.0) according to the following schedule: 2 ml; 1.6 ml; 1.2 ml; 1.6 ml; and 2 ml on days 1 through 5 respectively. On days 8 and 9, the rabbits were bled from the ear through an 18 gauge needle into 50 ml of cold saline (0.14M NaCl, 1.5 mM magnesium acetate, 5 mM KCl) containing 50–100 μl of heparin (Lipo-Hepin, Riker Laboratories, Inc. 1000 units/ml). The blood was filtered through sterile gauze and the cells were washed three times with cold saline.

Globin mRNA was extracted and purified from the rabbit reticulocytes prepared as described above by standard techniques involving lysing the reticulocytes, isolating RNA from the lysate and subsequently using immobilized oligo(dT) (i.e., which will hybridize to the poly(A) tail of mRNA) to isolate the mRNA component.

The reticulocytes were lysed in 2 mM $MgCl_2$, 1 mM EDTA, (pH 7.0), 1 mM β-mercaptoethanol (β-ME). The lysed suspension was centrifuged at 10,000×g for 10 minutes in order to sediment the insoluble components. The RNA was extracted from the supernatant with phenol-chloroform-isoamyl alcohol (24:24:1) saturated with STE (0.15M NaCl, 0.05M Tris-HCl (pH 7.2), 1 mM ethylenediamine tetraacetic acid or EDTA) containing 1% SDS (sodium dodecyl sulphate). The aqueous layer was adjusted to 0.2 M NaCl and the total RNA was precipitated with 2.5 volumes of absolute ethanol.

In order to isolate the poly(A) containing RNA component, the RNA precipitate was dissolved in 0.5 M NaCl, 0.01M Tris-HCl (pH 7.2), 0.5% SDS and chromatographed on oligo(dT)-cellulose (T3 Grade, Collaborative Research) pre-equilibrated with the same buffer. The oligo(dT) cellulose selectively binds polyadenylated RNA. The RNA which bound to the column was then eluted with buffer containing no salt (0.01M Tris, pH 7.2, 1% SDS). In order to further purify the mRNA from other contaminating RNAs, the eluted RNA was heated for 2 minutes at 65° C., adjusted to 0.5M NaCl and rechromatographed as previously described on oligo(dT)-cellulose. The RNA in the final eluate was precipitated with absolute ethanol as previously described.

The average sedimentation value for cellular mRNAs is approximately 18S. Globin mRNA sediments at 9S and is thus fractionated free from other cellular mRNAs by rate-zonal centrifugation on linear neutral sucrose gradients. The mRNA precipitate was resuspended in 0.01M Tris-HCl (pH 7.2), 1 mM EDTA, 0.2% SDS, heated for 2 minutes at 80° C. and fractionated by rate-zonal centrifugation in 5–20% neutral sucrose linear gradients containing 0.01M Tris HCl (pH 7.2) and 0.1 M NaCl (45,000×g at 5° C. for 6 hours in Beckman SW 50.1 rotor). The gradients were collected in 0.2 ml fractions by puncturing a hole in the bottom of the centrifuge tube and collecting the material by drops. The RNA content of the fractions was determined by measuring the absorbance at 260 nm. The 9S peak from the sucrose gradients contained both β- and α-globin mRNA. The β-globin mRNA sediments slightly faster than the α-globin mRNA; the β-globin mRNA was isolated for use in the following examples.

6.3. PREPARATION OF THE β-GLOBIN mRNA FOR DNA LINKER ATTACHMENT

In order to attach a ssDNA linker to the 5'-terminus of the β-globin mRNA molecules, the 5'-cap ($m^7G^{5'}ppp-^{5'}$) of the mRNA was removed; then the decapped 5'-terminus was modified to possess a monophosphate group. This was accomplished as follows: (1) the enzyme tobacco acid pyrophosphatase (TAP) was used to remove the 5'-cap; (2) the enzyme bacterial alkaline phosphatase (BAP) was used to remove the resultant 5'-mono- and di-phosphates and thus created a 5'-hydroxyl terminus on the mRNA molecule; and (3) the enzyme T4 polynucleotide kinase was used to transfer a monophosphate of ATP to the 5'-hydroxyl terminus. These procedures were previously described in the text and are discussed in detail in Sections 6.3.1. through 6.3.3. Finally, as explained in Section 6.4, T4 RNA Ligase was used to catalyze: (1) the ligation of the 5'-phosphoryl-terminus of the mRNA (donor) to the 3'-rA-hydroxyl-terminus of the ssDNA linkers (acceptor) prepared in Section 6.1.1, and (2) the ligation of the 5'-phosphoryl-terminus of the ssDNA linkers (donor) prepared in Section 6.1.2 to the 3'-hydroxyl terminus of the β-globin mRNA molecule (acceptor).

6.3.1. TOBACCO ACID PYROPHOSPHATASE TREATMENT OF β-GLOBIN mRNA

The enzyme tobacco acid pyrophosphatase (TAP) was isolated from cultured tobacco cells (*Nicotiana tabacum* var. Wisconsin 38; purchased from Alton Jones Cell Science Center, Lake Placid, N.Y.) and used for the enzymatic removal of the 5'-cap from the β-globin mRNA. (Lockard, et al., 1981, pages 229-251. In, Chirikjian & Papas, eds., *Gene Amplification and Analysis*, Vol. 2). TAP hydrolyzes the pyrophosphate bonds of the cap structure to yield a mixture of mRNA molecules with 5'-mono- and di-phosphate groups (Chinski, et al., 1976, Biochemistry 15: 2185). One unit of TAP is the amount of enzyme that releases 1 nmol of $^{32}$P from [γ-$^{32}$P]-ATP in 30 minutes at 37° C.

Briefly, 30 units of TAP was used to decap 20 μg $A_{260}$ units of β-globin mRNA in 200 μl of buffer containing 50 mM sodium acetate (pH 6.0). A final concentration of 0.01% diethyl pyrocarbon (DEP) was added to the TAP reaction to minimize the degradation of the β-globin mRNA; to this end 0.5 μl( of a freshly prepared 2% DEP solution was added to the 200 μl reaction mixture. The reaction mixture was incubated for 1 hour at 37° C. after which time an aliquot of 0.5M Tris-HCl (pH 8.4) was added to give a final concentration of 75 mM Tris-HCl (i.e., 1.5 μl( of 0.5M Tris-HCl was added to a 10 μl reaction mixture).

6.3.2. TREATMENT OF THE DECAPPED β-GLOBIN mRNA WITH BACTERIAL ALKALINE PHOSPHATASE

Bacterial Alkaline Phosphatase (BAP) catalyzes the removal of 5'-phosphate groups from either RNA or DNA. Treatment of the decapped B-globin mRNA with BAP yields a 5'-hydroxyl group on the mRNA molecule (Efstratiadis, et al., 1977, Nucleic Acids Res. 4: 4165).

Accordingly BAP (P.L. Biochemicals, Milwaukee, Wis.) was added to the final TAP reaction mixture of Section 6.3.1 at a final concentration of 0.1 unit/ml and the reaction was allowed to proceed for 45 minutes at 37° C. (One unit of BAP hydrolyzes one micromole of p-nitrophenylphosphate per minute at 25° C., pH 8.0.) The reaction mixture was immediately deproteinized by extracting the mRNA three times with phenol-chloroform-isoamyl alcohol containing 1% SDS as previously described. The mRNA, now decapped and containing a 5'-hydroxyl terminus, was precipitated with absolute ethanol.

6.3.3. T4 POLYNUCLEOTIDE KINASE TREATMENT OF β-GLOBIN mRNA

The enzyme, T4 polynucleotide kinase catalyzes the transfer of the γ-phosphate group of ATP to the 5'-hydroxyl terminus of a DNA or RNA molecule. As previously mentioned, the activity requirements for the enzyme include $Mg^{++}$ as a cofactor and dithiothreitol (DTT) as the reducing agent (Maxam and Gilbert, 1977, Proc. Natl. Acad. Sci., U.S.A. 74: 560). Thus a 5'-monophosphate was enzymatically added to the decapped and dephosphorylated β-globin mRNA through the use of ATP and T4 polynucleotide kinase (P.L. Biochemicals, Milwaukee, Wis.).

Approximately 15-20 μg of the β-globin mRNA (prepared in Section 6.3.2) was phosphorylated in a reaction mixture containing Kinase buffer consisting of: 0.05M Tris-HCl (pH 7.5), 0.01M $MgCl_2$, 0.001M DTT, and 2-5 units T4 polynucleotide kinase in a total volume of approximately 0.1 ml. The reaction was allowed to proceed for 30 minutes at 37° C. after which time the RNA was extracted three times with phenol-chloroform-isoamyl alcohol, as previously described, and ethanol precipitated. The decapped β-globin mRNA, now containing a 5'-monophosphate group, was now ready for ligation to the ssDNA linker groups prepared in Section 6.1.

6.4. T4 RNA LIGASE MEDIATED COVALENT LINKAGE OF ssDNA LINKERS TO β-GLOBIN mRNA

The chemically synthesized ssDNA linkers prepared in Section 6.1 were ligated to the β-globin mRNA molecule using T4 RNA ligase. The enzyme, T4 RNA ligase catalyzes the ATP-dependent ligation of a 5'-phosphoryl-terminated nucleic acid "donor" to a 3'-hydroxyl-terminated nucleic acid "acceptor". Unlike DNA ligase, a template strand is not needed. Substrates for the enzyme include single-stranded RNA and DNA as well as 3',5'-biphosphate mononucleosides (pNp) (England, et al., 1977, Proc. Natl. Acad. Sci., U.S.A. 74: 4839-4842).

T4 RNA ligase can efficiently join RNA molecules of almost any size and DNA molecules of almost any size albeit the latter are joined to one another at a slower rate; DNA molecules are joined at about one two-hundredth the rate of RNA molecules. This differential rate is due to the superior effectiveness of the 3'-oligoribonucleotide hydroxyl acceptor (McCoy and Gumport, 1980, Biochem. 19: 635-642).

In the T4 RNA ligase mediated linkage described in the following sections (6.4.1. and 6.4.2.), the chemically synthesized DNA linkers prepared in Section 6.1.1 provide the acceptors for the ligase reaction. The presence of a 3'-ribonucleotide (rA) on these modified DNA linkers provides an efficient 3'-hydroxyl acceptor so that the RNA ligase mediated linkage will be driven at its optimal rate. The β-globin mRNA molecules, prepared in Section 6.3.3 provide the necessary donor 5'-phosphate in the RNA ligase mediated reaction.

The attachment of ssDNA linkers prepared in Section 6.1.2 to the 3'-termini of the β-globin mRNA was similarly mediated by T4 RNA ligase. In this reaction, the 3'-hydroxyl of the β-globin mRNA provides the RNA acceptor which drives the reaction at an optimal rate. The DNA-linkers prepared in Section 6.1.2. provide the necessary donor 5'-phosphate in the RNA ligase mediated reaction.

In the following examples, the T4 RNA ligase used was purchased from P.L. Biochemicals (Milwaukee, Wis.). One unit of activity catalyzes the formation of lnmol of phosphatase-resistant $^{32}$P in 30 minutes at 37° C. with 5'-$^{32}$P-oligo(rA)n as substrate.

6.4.1. JOINING THE SYNTHETIC DNA LINKER TO THE 5'-END OF THE β-GLOBIN mRNA

T4 RNA ligase was employed to enzymatically join the synthetic DNA linker prepared in Section 6.1.1 to the 5'-terminus of the de-capped, phosphorylated β-globin mRNA. This synthetic linker encodes the EcoRI restriction site and contains a 5'-hydroxyl group and a 3'-ribonucleotide (adenylic acid); thus, the linker sequence is: 5'-EcoRI.rA-3'. The 5'-hydroxyl group of the DNA linker rendered the linker functional only as an acceptor molecule (donor molecules contain 5'-phosphates) and prevented the attachment of one linker to another linker. A molar excess of the ssDNA linker was added to the reaction mixture.

The reaction mixture contained 1 μg of synthetic DNA linker, 0.3 μg of β-globin mRNA, and approximately 3 units of T4 RNA ligase in 10 μl of RNA ligase buffer which consisted of: 50 mM HEPES, pH 8.0, 10 mM MnCl$_2$, 10 mM DTT, 10 μM ATP, and 50 μg/ml bovine serum albumin. The reaction mixture was incubated for 5 hours at 15° C. and then ethanol precipitated two times. In order to prevent aggregation and ethanol precipitation of the unbound DNA linkers, the precipitate was heated for 2 minutes at 65° C. prior to the second ethanol precipitation.

6.4.2. JOINING OF THE SYNTHETIC DNA LINKER TO THE 3'-END OF THE β-GLOBIN mRNA

T4 RNA ligase was also employed to enzymatically join a synthetic DNA linker to the 3'-terminus of the β-globin mRNA molecule. The DNA linker prepared in section 6.1.2 encodes the BamHI and EcoRI restriction sites as follows: 5'-BamHI.EcoRI-3' and was phosphorylated at its 5'-terminus using polynucleotide kinase.

In order to ligate the 5'-phosphorylated DNA linker to the 3'-hydroxyl terminus of the β-globin mRNA, the oligonucleotide mRNA precipitate of Section 6.4.1 (approximately 0.3 μg) was resuspended in 10 μl of the final reaction mixture of Section 6.1.2 which contained approximately 1 μg of the 5'-phosphorylated BamHI.EcoRI-3' ssDNA linker. Approximately 3 units of T4 RNA ligase was added and the reaction was allowed to incubate for 5 hours at 15° C. after which time the oligonucleotide product was ethanol precipitated as previously described.

6.5 CLONING OF β-GLOBIN mRNA

After the ligation reactions (above) the mRNA was converted into a double-stranded form by synthesizing a complementary DNA strand (cDNA); this should result in a cDNA/mRNA hybrid molecule that is flanked by double stranded DNA sequences which encode restriction enzyme sites (Section 6.5.1).

The resulting cDNA/mRNA hybrid was then treated with the restriction enzymes EcoRI and BamHI to create cohesive termini (Section 6.5.2). These enzymes will not recognize and cleave the RNA/DNA hybrid. Thus, in the event that EcoRI or BamHI sites exist within the β-globin mRNA these RNA/DNA hybrid sites will be immune from enzyme cleavage.

After cleavage, the cDNA/mRNA hybrid was inserted into a DNA vector which was also cleaved to generate complementary cohesive termini; a derivative of the plasmid pBR322 was chosen since it contains appropriately positioned EcoRI and BamHI sites. Once inserted into the cloning vector, the vector was utilized to transform a suitable host (Section 6.5.4.).

6.5.1. cDNA SYNTHESIS

The single-stranded cDNA copy of the flanked β-globin mRNA molecule was synthesized using the enzyme, reverse transcriptase. A synthetic DNA molecule which is complementary to the 3'-flanking sequence of the β-globin in RNA molecule (e.g., the single-stranded BamHI.EcoRI sequence) was used as a primer for the reverse transcriptase synthesis of the flanked mRNA template.

The β-globin mRNA precipitate of Section 6.4.2. (approximately 0.3 μg template RNA) was resuspended in 50 μl (i.e., at a concentration of 6 μg/ml template RNA) of the following reaction buffer for reverse transcriptase synthesis of cDNA: 50 mM Tris-HCl (pH 8.0), 8 mM MgCl$_2$, 75 mM β-ME, 28 mM KCl, and 400 μM of each deoxynucleotide triphosphate (all four dNTPS). The following components were added to this buffer: 200 units/ml highly purified reverse transcriptase, and 20 μg/ml DNA primer. (One unit is the amount of enzyme which incorporates one pmol of deoxythymidine-5'-triphosphate into acid precipitable product in 1 minute at 37° C. using poly(rA).oligo (dT)$_{12-18}$ as template.) The reaction mixture was incubated at 37° C. for 90 minutes after which time the reaction was terminated by the addition of EDTA to a final concentration of 10 mM. The mixture was then heated at 65° C. for 10 minutes and sodium chloride was added to a final concentration of 300 mM. The cDNA/mRNA hybrid thus formed was ethanol precipitated as previously described.

6.5.2. RESTRICTION ENDONUCLEASE CLEAVAGE OF THE RNA/DNA HYBRID

The cDNA/mRNA hybrid was resuspended in approximately 20 μl of Restriction Enzyme Buffer (10 mM Tris-HCl, pH 7.4, 60 mM NaCl, 10 mM MgCl$_2$, 1 mM DTT). The hybrid was simultaneously digested with 4 units of EcoRI and 4 units of BamHI (Bethesda Research Laboratories, Inc., Rockville, Md.) during a 60 minute incubation at 37° C. One unit of restriction enzyme is defined as the amount of enzyme required to completely digest 1.0 μg of lambda phage, or equivalent, DNA in one hour, at appropriate temperature, in a 50 μl volume. The reaction mixture was then deproteinized by phenol extraction as previously described and the cDNA/mRNA hybrid was ethanol precipitated.

6.5.3 RESTRICTION ENDONUCLEASE CLEAVAGE OF THE DNA CLONING VECTOR

The DNA cloning vector chosen in the example of the present invention is pBR322 carrying resistance genes for both ampicillin and tetracycline and containing single EcoRI and BamHI restriction cleavage sites. After cleavage with the restriction enzyme BamHI, the vector is treated with the enzyme bacterial alkaline phosphatase (BAP) which removes the 5'-phosphate groups. The presence of 5'-hydroxyl groups prevents subsequent ligation of vector to vector and therefore favors ligation of the cDNA/mRNA hybrid to the vector.

The vector was first cleaved with BamHI using the same reaction conditions described previously. Approximately 1 unit/ml BAP was then added to the mixture, and incubation was allowed to continue at 37° C. for 45 minutes after which time the reaction was stopped by phenol extraction as previously described and the cleaved DNA vector was ethanol precipitated.

The plasmid was then cleaved with EcoRI using the same reaction conditions as described previously. The double digestion resulted in the creation of two linear plasmid fragments: approximately 3989 bp and 373 bp each. The entire digest was then run on a 1% Agarose gel (Bethesda Research Laboratories, Inc., Rockville, MD) as described in *Advanced Bacterial Genetics,* Davis, Botstein, Roth, p. 148–152, Cold Spring Harbor (1980). The larger 3989 bp fragment was electroeluted from the gel and further purified by DEAE column chromatography.

The resulting cleaved pBR322 vector was a linear molecule of 3989 bp flanked by EcoRI and BamHI cohesive termini. These sequence-specific ends allow for the directional cloning of the β-globin cDNA/mRNA hybrid molecule. After cleavage the vector carried the marker gene for ampicillin resistance but the tetracycline resistance gene was destroyed by the removal of the 373 bp fragment.

6.5.4 INSERTION OF THE B-GLOBIN GENE INTO THE DNA CLONING VECTOR

The cleaved plasmid and the β-globin cDNA/mRNA hybrid were mixed to allow base-pair hybridization or annealing. T4 DNA ligase (Bethesda Research Laboratories, Inc., Rockville, Md) was employed to covalently join the β-globin cDNA/mRNA hybrid (prepared in Section 6.5.2) to the pBR322 fragment (prepared in Section 6.5.3) by incubating 6.6 μg/ml vector with 1 μg/ml cDNA/mRNA hybrid in 30 μl buffer consisting of: 66 mM Tris-HCl, (pH 7.4), 6.6 mM $MgCl_2$, 10 mM DTT, 1 μM ATP and 1-3 units of T4 DNA ligase for 10-18 hours at 23° C.

The resultant mixture which consisted of recombinant plasmids that carry the ampicillin resistance gene as a marker function, was then used to transform an *E. coli* K12 derivative by standard procedures (see Maniatis et al., 1982, Molecular Cloning, A Laboratory Manual, Cold Spring Harbor Laboratory, pages 247-255). The transformants were plated on agar containing ampicillin. Successfully transformed *E. coli* are rendered ampicillin resistant and thus were selected based on their ability to grow on the ampicillin containing agar (see Maniatis et al., 1982, Molecular Cloning, A Laboratory Manual, Cold Spring Harbor Laboratory, pages 55-73).

6.6. DETECTION OF CLONES CONTAINING cDNA SEQUENCES

The ampicillin-resistant bacteria were replated in duplicate and one set used for the detection of cloned sequences by standard colony hybridization procedures (Grunstein M. and Hogness, 1975, Proc. Natl. Acad. Sci., U.S.A. 72: 3961-3965). The radiolabelled DNA probe used in these hybridizations was prepared by synthesizing the cDNA copy of the original β-globin mRNA using reverse transcriptase under the following conditions: 50 mM Tris-HCl (pH 8.0), 10 mM $MgCl_2$, 75 mM β-ME, 200 μM of each deoxynucleotide- triphosphate dGTP, dCTP, and dTTP, and 200 μCi α[$^{32}$P]ATP 150 μg/ml calf thymus primer, 40 μg/ml template RNA (here, β-globin mRNA), and 100 units/ml reverse transcriptase. After 60 minutes at 37° C., the reaction was terminated by the addition of EDTA (10 mM), boiled for 2 minutes, and treated with 50 μg/ml RNAse A at 37° C. for 20 minutes in order to remove the mRNA component. The resultant single-stranded radiolabelled cDNA was phenol extracted as previously described and ethanol precipitated several times. Approximately 2% of the clones were positive for β-globin sequences by colony hybridization.

6.7. CHARACTERIZATION OF THE RECOMBINANT PLASMIDS CONTAINING THE β-GLOBIN GENE

Plasmid DNA from hybridization positive colonies was isolated and the size of the insert was determined by restriction enzyme analysis using gel electrophoresis. These methods, including restriction endonuclease mapping of the β-globin gene were accomplished using standard techniques (Bolivar and Backman, 1979, Methods in Enzymology 68: 245-267). Since the β-globin gene has been previously cloned and its restriction map determined (Efstratiadis, et al., 1975, Cell 4: 367), cloning of the β-globin gene provided an excellent test for our RNA ligase mediated directional cloning procedure.

Results from this data confirmed that nearly full length β-globin mRNA was successfully cloned. The data from clones screened to date indicate that such cloning occurred via the circularization mechanism described in the text.

7. EXAMPLE: MOLECULAR CLONING OF RIFT VALLEY FEVER VIRUS RNA

Rift Valley Fever virus (RVF virus) is a member of the Bunyaviridae group. These viruses have a single-stranded, three segment, negative sense RNA genome with a total molecular weight between 4 to $6 \times 10^6$ daltons. The viral RNA segments are designated according to their sizes: large (L), medium (M), small (S). The three RNA species of RVF virus have the following molecular weights: L, $2.7 \times 10^6$; M, $1.7 \times 10^6$; and S, $0.6 \times 10^6$.

In the example which follows, a portion of the M species of the RVF virus was cloned by: (1) attaching an oligodeoxyribonucleotide linker encoding an EcoRI recognition sequences to the 3'-terminus of the RVF M-RNA molecule; (2) synthesizing cDNA using reverse transcriptase to form a cDNA/RNA hybrid molecule; (3) cleaving the cDNA/RNA hybrid molecule with BamHI and EcoRI to create cohesive ends; (4) annealing and ligating the cDNA/RNA hybrid molecule to pBR322 which had been previously cleaved with EcoRI and BamHI; and (5) using the ligation mix to transform E. coli.

7.1. SNYTHESIS OF THE ssDNA LINKER FOR ATTACHMENT TO THE 3'-TERMINUS OF THE RVF M-RNA

The oligodeoxyribonucleotide linker which was attached to the 3'-terminus of the RVF M-RNA molecule was synthesized as described in Section 6.1., encoded the sequence described in Section 6.1.1. (i.e., EcoRI-rA) and was phosphorylated using T4 polynucleotide kinase as described in Section 6.1.2.

7.2. T4 RNA LIGASE MEDIATED ATTACHMENT OF ssDNA LINKER TO RVF M-RNA

The synthetic DNA linker described in Section 6.1.1. (i.e., EcoRI-rA) was ligated to the 3'-termini of a mixture of RVF M-RNA fragments as follows:

A mixture of RVF M-RNA fragments was ethanol-precipitated and resuspended in 10 μl of the final T4 polynucleotide kinase reaction mixture of Section 7.1. which contained approximately 1 μg of the 5'-phosphorylated EcoRI-rA ssDNA linker. Then, approximately 3 units of T4 RNA ligase (P.L. Biochemicals, Milwaukee, Wis.) was added and the reaction was incubated for 44 hours at 15° C. after which time the oligonucleotide product was ethanol-precipitated.

7.3. CLONING OF RVF M-RNA

After the ligation reaction described above, the RVF M-RNA-EcoRI-rA was converted to a double-stranded form by synthesizing a cDNA strand using reverse transcriptase. To this end the RVF M-RNA-EcoRI-rA precipitate of Section 7.2. was resuspended in 50 @ of the reaction buffer described in Section 6.5.1. and the entire reaction was performed as described in that section.

The resulting cDNA/RNA hybrid was then treated with EcoRI and BamHI in order to create cohesive ends. To this end the cDNA/RNA hybrid was simultaneously digested with EcoRI and BamHI as described in Section 6.5.2. Then the cDNA/RNA hybrid was annealed and ligated (as described in Section 6.5.4.) to pBR322 which had previously been cleaved with EcoRI and BamHI (as described in Section 6.5.3.).

The resulting ligation mixture was used to transform *E. coli* K12 and clones were screened and identified as described in Section 6.6. Recombinant vectors isolated from positive colonies were characterized by restriction mapping as described in Section 6.7.

Results from this data confirmed that a 250 b.p. RVF M-RNA sequence was successfully cloned into the pBR322 vector. The 5′-terminus of the cloned insert consisted of a BamHI site which is located within the RVF M-RNA species itself. The presence of the EcoRI-rA linker ligated to the 3′-terminus at the cloned insert was verified by DNA sequencing (Maxam and Gilbert, 1980, Methods in Enzymology, 65: 497–559), thus proving that linker ligation to the RVF M-RNA using T4 RNA ligase was successful.

It is apparent that many modifications and variations of the invention as set forth may be made without departing from the spirit and scope thereof. The specific embodiments described are given by way of example only and the invention is limited only by the appended claims. Indeed, various modifications of the invention in addition to those shown and described herein will become apparent to those skilled in the art from the following description and accompanying drawings. Such modifications are intended to fall within the scope of the appended claims.

What is claimed is:

1. A method for the insertion of a single-stranded RNA sequence into a cloning vector, comprising: annealing both termini of the single-stranded RNA sequence with a linear double-stranded cloning vector having single-stranded termini complementary to both termini of the single-stranded RNA sequence to form an annealed product, in which the complementary termini of the single-stranded RNA sequence where formed by attaching oligonucleotide linkers to the RNA sequence by means of an RNA ligase.

2. The method according to claim 1 wherein said RNA ligase is T4 RNA ligase.

3. The method according to claim 2 wherein the oligonucleotide linker attached to the 3′-terminus of the RNA sequence is composed of DNA.

4. The method according to claim 2 wherein the oligonucleotide linker attached to the 3′-terminus of the RNA sequence is composed of RNA.

5. The method according to claim 2 wherein the oligonucleotide linker attached to the 3′-terminus of the RNA sequence is composed of a mixture of DNA and RNA.

6. The method according to claim 3 wherein the DNA linker is single-stranded.

7. The method according to claim 3 wherein the DNA linker is double-stranded.

8. The method according to claim 2 wherein the oligonucleotide linker attached to the 5′-terminus of the RNA sequence is composed of a mixture of DNA and RNA such that the 3′-terminus of the oligonucleotide linker is a ribonucleotide.

9. The method according to claim 2 wherein the oligonucleotide linker attached to the 5′-terminus of the RNA sequence is composed of RNA.

10. The method according to claim 8 wherein the oligonucleotide linker is single-stranded.

11. The method according to claim 8 wherein the oligonucleotide linker is double-stranded.

12. The method according to claim 1 wherein said oligonucleotide linkers contain a DNA sequence encoding a restriction endonuclease recognition site.

13. The method according to claim 12 wherein the oligonucleotide linker sequences are double-stranded and are cleaved with a restriction endonuclease such that a cohesive end is generated prior to annealing with the cloning vector.

14. The method according to claim 1 further comprising the step of subjecting the annealed product to an enzyme capable of forming a covalent 3′–5′ phosphodiester bond between the single-stranded RNA sequence and the cloning vector to form a recombinant molecule.

15. The method according to claim 1 further comprising the step of converting the RNA sequence to a cDNA/RNA hybrid molecule.

16. A method for cloning an RNA sequence, comprising:

(a) inserting the single-stranded RNA sequence into a cloning vector by annealing both termini of the single-stranded RNA sequence with a linear double-stranded cloning vector having single-stranded termini complementary to both termini of the single-stranded RNA sequence to form an annealed product, in which the complementary termini of the single-stranded RNA sequence were formed by attaching oligonucleotide linkers to the RNA sequence by means of an RNA ligase;

(b) converting the RNA sequence to a cDNA/RNA hybrid to form a recombinant molecule;

(c) introducing the recombinant molecule containing the cDNA/RNA hybrid into a compatible unicellular organism capable of replicating the recombinant molecule to form transformants; and (d) growing the transformants under appropriate nutrient conditions.

17. A method for the insertion of a single-stranded RNA sequence into a cloning vector, comprising: annealing the single-stranded RNA sequence with a linear double-stranded cloning vector having a 5′-single-stranded terminus complementary to the 5′-terminus of the single-stranded RNA sequence to form an annealed product, in which the 5′-complementary terminus of the single-stranded RNA sequence was formed by attaching an oligonucleotide linker to the single-stranded RNA sequence by means of an RNA ligase.

18. The method according to claim 17 wherein said RNA ligase is T4 RNA ligase.

19. The method according to claim 18 wherein said oligonucleotide linker attached to the 5′-terminus of the RNA sequence is composed of a mixture of DNA and RNA such that the 3'-terminus of the oligonucleotide linker is a ribonucleotide.

20. The method according to claim 18 wherein said oligonucleotide linker attached to the 5'-terminus of the RNA sequence is composed of RNA.

21. The method according to claim 17 further comprising the step of subjecting the annealed product to an enzyme capable of forming a covalent 3'-5'-phosphodiester bond between the single-stranded RNA sequence and the cloning vector.

22. The method according to claim 21 wherein said RNA ligase is T4 RNA ligase and a covalent bond is formed between the 3'-terminus of the single-stranded RNA sequence and the cloning vector to form a recombinant molecule.

23. The method according to claim 22 further comprising the step of converting the RNA sequence to a cDNA/RNA hybrid molecule.

24. A method for cloning an RNA sequence, comprising:
  (a) inserting the single-stranded RNA sequence into a cloning vector by annealing the single-stranded RNA sequence with the linear double-stranded cloning vector having a 5'-single-stranded terminus complementary to the 5'-terminus of the single-stranded RNA sequence to form an annealed product;
  (b) forming a covalent bond between the 3'-terminus of the single-stranded RNA sequence and the cloning vector by means of an RNA ligase, to form a recombinant molecule;
  (c) converting the RNA sequence of the recombinant molecule to a cDNA/RNA hybrid to form a double-stranded recombinant molecule;
  (d) introducing the double-stranded recombinant molecule containing the cDNA/RNA hybrid into a compatible unicellular organism capable of replicating the recombinant molecule to form transformants; and
  (e) growing the transformants under appropriate nutrient conditions.

25. A method for the insertion of a single-stranded RNA sequence into a cloning vector, comprising:
  (a) annealing the 3'-terminus of the single-stranded RNA sequence with a linear double-stranded cloning vector having a first 3'-single-stranded terminus complementary to the 3'-terminus of the single-stranded RNA sequence and a second 3'-single-stranded terminus composed of RNA; and
  (b) forming a covalent bond between the 5'-terminus of the single-stranded RNA sequence and the second 3'-terminus of the cloning vector by means of an RNA ligase.

26. The method according to claim 25 wherein said first 3'-single-stranded terminus of the cloning vector is formed by ligating an oligonucleotide linker to a linear double-stranded cloning vector.

27. The method according to claim 25 wherein said first 3'-single-stranded terminus of the cloning vector is formed by attaching nucleotides to a linear double-stranded cloning vector by means of terminal deoxynucleotidyl transferase.

28. The method according to claim 25 wherein said second 3'-single-stranded terminus of the cloning vector is formed by attaching RNA to a linear double-stranded cloning vector by means of terminal deoxynucleotidyl transferase.

29. The method according to claim 25 wherein said RNA ligase is T4 RNA ligase and a covalent bond is formed between the 5'-terminus of single-stranded RNA sequence and said second 3'-terminus of the cloning vector to form a recombinant molecule.

30. The method according to claim 29 further comprising the step of converting the RNA sequence to a cDNA/RNA hybrid molecule.

31. A method for cloning an RNA sequence comprising:
  (a) inserting the single-stranded RNA sequence into a cloning vector by annealing the single-stranded RNA sequence with the cloning vector having a first 3'-single-stranded terminus complementary to the 3'-terminus of the single-stranded RNA sequence, and a second 3'-single-stranded terminus composed of RNA to form an annealed product;
  (b) forming a covalent bond between the 5'-terminus of the single-stranded RNA sequence and the second 3'-terminus of the cloning vector by means of an RNA ligase to form a recombinant molecule;
  (c) converting the RNA sequence of the recombinant molecule to a cDNA/RNA hybrid to form a double-stranded recombinant molecule;
  (d) introducing the double-stranded recombinant molecule containing the cDNA/RNA hybrid into a compatible unicellular organism capable of replicating the recombinant molecule to form transformants; and
  (e) growing the transformants under appropriate nutrient conditions.

32. A method for the insertion of a single-stranded RNA sequence into a cloning vector, comprising:
  (a) circularizing the RNA sequence by means of an enzyme capable of ligating RNA;
  (b) synthesizing a cDNA strand which is complementary to the circularized RNA sequence to form a CDNA/RNA circular hybrid molecule;
  (c) ligating the cDNA strand and removing the RNA portion of the circular hybrid molecule;
  (d) syntesizing a second DNA strand which is complementary to the cDNA strand to form a circular double-stranded DNA molecule;
  (e) cleaving the circular double-stranded DNA molecule by means of a restriction endonuclease capable of cleaving said circular DNA to produce a linear double-stranded DNA molecule having single-stranded termini; and
  (f) annealing the linear double-stranded DNA molecule with a linear double-stranded cloning vector having complementary single-stranded termini to form an annealed product.

33. The method according to claim 32 wherein said enzyme capable of ligating RNA is T4 RNA ligase.

34. The method according to claim 32 further comprising the step of subjecting the annealed product to an enzyme capable of forming covalent 3'-5' phosphodiester bonds between the double-stranded DNA molecule and the double-stranded cloning vector to form a recombinant molecule.

35. A method for cloning an RNA sequence, comprising:
  (a) circularizing the RNA sequence by means of an enzyme capable of ligating RNA;
  (b) synthesizing a cDNA strand which is complementary to the circularized RNA sequence to form a cDNA/RNA circular hybrid molecule;

(c) ligating the cDNA strand and removing the RNA portion of the circular hybrid molecule;
(d) synthesizing a second strand of DNA which is complementary to the cDNA strand to form a circular double-stranded DNA molecule;
(e) cleaving the circular double-stranded DNA molecule by means of a restriction-endonuclease capable of cleaving said circular DNA to produce a linear double-stranded molecule having single-stranded termini;
(f) annealing the linear double-stranded DNA molecule with a linear double-stranded cloning vector having complementary single-stranded termini to form an annealed product;
(g) forming a covalent 3'-5'phosphodiester bond between the double-stranded DNA molecule and the double-stranded cloning vector to form a recombinant molecule;
(h) introducing the recombinant molecule into a compatible unicellular organism capable of replicating the recombinant molecule to form transformants; and
(i) growing said transformants under appropriate nutrient conditions.

36. A method for the insertion of a single-stranded RNA sequence into a cloning vector, comprising:
(a) attaching to said RNA sequence an oligonucleotide linker by means of an enzyme capable of ligating RNA to form an RNA-linker product, wherein said linker contains a deoxyribonucleotide sequence encoding a restriction endonuclease recognition site and a 3'-terminal ribonucleotide;
(b) circularizing the RNA-linker product by means of an enzyme capable of ligating RNA;
(c) synthesizing a cDNA strand which is complementary to the circularized RNA sequence to form a cDNA/RNA circular hybrid molecule containing a duplex DNA site that encodes a restriction enzyme recognition site;
(d) cleaving the circular hybrid molecule at said duplex DNA site by means of a restriction endonuclease capable of cleaving said duplex DNA site to form a linear hybrid molecule having single-stranded termini; and
(e) annealing the linear hybrid molecule with a linear double-stranded cloning vector having complementary termini to form an annealed product.

37. The method according to claim 36 wherein said enzyme is T4 RNA ligase.

38. The method according to claim 36 further comprising the step of subjecting the annealed product to an enzyme capable of forming covalent 3'-5'phosphodiester bonds between the hybrid molecule and the double-stranded cloning vector to form a recombinant molecule.

39. A method for cloning an RNA sequence, comprising:
(a) attaching to said RNA sequence an oligonucleotide linker by means of an enzyme capable of ligating RNA to form an RNA-linker product, wherein said linker contains a deoxyribonucleotide sequence encoding a restriction endonuclease recognition site and a 3'-terminal ribonucleotide;
(b) circularizing the RNA-linker product by means of an enzyme capable of ligating RNA;
(c) synthesizing a cDNA strand which is complementary to the circularized RNA sequence to form a cDNA/RNA circular hybrid molecule containing a duplex DNA site that encodes a restriction enzyme recognition site;
(d) cleaving the circular hybrid molecule at said duplex DNA site by means of a restriction endonuclease capable of cleaving said duplex DNA site to form a linear hybrid molecule having single-stranded termini;
(e) annealing the linear hybrid molecule with a linear double-stranded cloning vector having complementary single-stranded termini to form an annealed product;
(f) forming a covalent 3'-5'phosphodiester bond between the hybrid molecule and the double-stranded cloning vector to form a recombinant molecule;
(g) introducing the recombinant molecule into a compatible unicellular organism capable of replicating the recombinant molecule to form transformants; and
(h) growing said transformants under IIIIIappropriate nutrient conditions.

* * * * *